US007393940B2

(12) United States Patent
Sampson et al.

(10) Patent No.: US 7,393,940 B2
(45) Date of Patent: Jul. 1, 2008

(54) SCREENING METHODS AND SEQUENCES RELATING THERETO

(75) Inventors: Julian R. Sampson, Llandaff (GB); Jeremy P. Cheadle, Bichgrove (GB)

(73) Assignee: University of Wales, Wales (GB)

( * ) Notice: Subject to any disclaimer, the term of this patent is extended or adjusted under 35 U.S.C. 154(b) by 0 days.

(21) Appl. No.: 11/247,968

(22) Filed: Oct. 11, 2005

(65) Prior Publication Data
US 2006/0183134 A1 Aug. 17, 2006

Related U.S. Application Data

(63) Continuation-in-part of application No. PCT/GB03/01656, filed on Apr. 16, 2003.

(30) Foreign Application Priority Data
Apr. 10, 2003 (GB) ................................. 0308241.9

(51) Int. Cl.
*C07H 21/04* (2006.01)
(52) U.S. Cl. ..................................... 536/23.1; 536/23.5
(58) Field of Classification Search ........................ None
See application file for complete search history.

(56) References Cited

U.S. PATENT DOCUMENTS

| 6,013,473 | A | 1/2000 | Wei |
| 6,051,222 | A | 4/2000 | Wei |
| 6,639,063 | B1 | 10/2003 | Edwards et al. |

FOREIGN PATENT DOCUMENTS

| WO | WO 97/33903 | 9/1997 |
| WO | WO 03/014390 | 2/2003 |

OTHER PUBLICATIONS

Product #1256, Random Primer 24, New England Biolabs Catalog (1998-1999) p. 121.*
Martin et al. Lemur catta clone LB2-195A23, Working Draft Sequence, 23 ordered pieces. GenBank Accession No. AC118575 (2002).*
Al-Tassan et al., "Inherited variants of MYH associated with somatic G:C→T:A mutations in colorectal tumors", *Nature Genetics*, Feb. 2002, 30:227-232.
Audebert et al., "Effect of single mutations in the OGG1 gene found in human tumors on the substrate specificity of the Ogg1 protein", *Nucleic Acids Research*, 2000, 28(14):2672-2678.
Boiteux et al., "The Human OGG1 Gene: Structure, Functions, and Its Implication in the Process of Carcinogenesis", *Archives of Biochemistry and Biophysics*, May 1, 2000, 377(1):1-8.

Fearnhead et al., "The ABC of APC", *Human Molecular Genetics*, 2001, 10(7):721-733.
Gu et al., "Differential DNA recognition and glycosylase activity of the native human MutY homolog (hMYH) and recombinant hMYH expressed in bacteria", *Nucleic Acids Research*, 2001, 29(12):2666-2674.
Jones et al., "Biallelic germline mutations in MYH predispose to multiple colorectal adenoma and somatic G:C→ T: A mutations", *Human Molecular Genetics*, Nov. 1, 2002, 11(23):2961-2967.
Nakabeppu, Yusaku, "Molecular genetics and structural biology of human MutT homolog, MTH1", *Mutation Research*, 2001, 477:59-70.
Ohtsubo et al., "Identification of human MutY homolog (hMYH) as a repair enzyme for 2-hydroxyadenine in DNA and detection of multiple forms of hMYH located in nuclei and mitochondria", *Nucleic Acids Research*, 2000, 28(6):1355-1364.
Shinmura et al., "Infrequent Mutations of the hOGG1 Gene, That Is Involved in the Excision of 8-Hydroxyguanine in Damaged DNA, in Human Gastric Cancer", *Jpn. J. Cancer Research*, Aug. 1998, 89:825-828.
Shinmura et al., "Somatic mutations and single nucleotide polymorphisms of base excision repair genes involved in the repair of 8-hydroxyguanine in damaged DNA", *Cancer Letters*, 2001, 166:65-69.
Slupska et al., "Cloning and Sequencing a Human Homolog (hMYH) of the *Escherichia coli* mutY Gene Whose Function Is Required for the Repair of Oxidative DNA Damage", *Journal of Bacteriology*, Jul. 1996, 178(13)3885-3892.
Sugimura et al., "hOGG1 Ser326Cys Polymorphism and Lung Cancer Susceptibility", *Cancer Epidemiology, Biomarkers & Prevention*, Aug. 1999, 8:669-674.
Tsuzuki et al., "Analysis of MTH1 gene function in mice with targeted mutagenesis", *Mutation Research*, 2001, 477:71-78.
Wikman et al., "hOGG1 Polymorphism and Loss of Heterozygosity (LOH): Significance for Lung Cancer Susceptibility in a Caucasian Population", *Int. J. Cancer*, 2000, 88:932-937.

* cited by examiner

*Primary Examiner*—Kenneth R. Horlick
*Assistant Examiner*—David C. Thomas
(74) *Attorney, Agent, or Firm*—Andrew Gibbs; Jay Z. Zhang; Myriad I.P. Dept.

(57) ABSTRACT

A screening method for identifying an individual having a pre-disposition towards having a cancer is disclosed, which screening method comprises the steps of:
(a) obtaining a test sample comprising a nucleotide sequence comprised in the MYH gene of the individual or an amino acid sequence of a polypeptide expressed thereby; and
(b) comparing a region of the test sample sequence with the corresponding region of the wild type sequence,
whereby a difference between the test sample sequence and the wild type sequence signifies that the individual is pre-disposed to having the cancer; and wherein the difference comprises a specified variation.

31 Claims, No Drawings

SEQUENCE LISTING

<160> NUMBER OF SEQ ID NOS: 36

<210> SEQ ID NO 1
<211> LENGTH: 10949
<212> TYPE: DNA
<213> ORGANISM: Homo sapiens

<400> SEQUENCE: 1

| | | | | | |
|---|---|---|---|---|---|
| atgacaccgc | tcgtctcccg | cctgagtcgt | ctgtgggtac | gctggacttg cggtccgtct | 60 |
| cctggcgcgg | ttcaggcagt | cggggatggg | gcggggtctc | gccgtcgggt cgccgatggg | 120 |
| tcgaacttcc | gttcagacgt | cccgggtccg | gcgcggggaa | ggcagcctgg cgcgcgctaa | 180 |
| ttgcctattg | gcctgtgctg | ccggctcgca | gcccgggtgg | acccgagcca cgcccctgg | 240 |
| agtgcgccgg | aaagccgggc | gcgctagagc | tcgcgggagg | taatctttct ctcctgctct | 300 |
| cgcggcggga | acgcggggcc | tccgtgttct | gctgtcttca | tcagcgtggg ccgcgggtag | 360 |
| cgggtagtgg | ggtggctggg | tttgggcttt | ccagagaagg | tgacgctgcc tgagctgagc | 420 |
| ttaaagcacg | cccaggagtt | agactaggag | agggtcgtgt | gggggaaaga agggcgttct | 480 |
| gggcatcggt | aaattcccag | agaggatgga | gagctcagtg | atctccagaa agtgaaagag | 540 |
| gcggggagtg | ggccatcgga | ggaggctgcc | caggtgtaa | gagcgaccga ttggtaggga | 600 |
| agcttttgta | ataatccaat | caagtgataa | tgtgaacttg | aattaaggct ggcagtatgg | 660 |
| atggcgagga | agggacaaat | tgtgaagcag | ctaggcggta | tagtcgacct agagggtgat | 720 |
| tgaatttgaa | agaggttcct | aggccgggcg | cggtggctca | cgcctgtaat cccagcactt | 780 |
| tgggaggccg | aggcgggcgg | attacctgag | gtccggagtt | caaaaccagc ctggccaaca | 840 |
| tggtgaaacc | ccgtctctac | taaaagtaca | aaaaaatta | gctgggtatg gtgcgggcgc | 900 |
| ctgtaatccc | actactgggg | aggctgaggc | aggagaatcg | cttgaacctg ggaggcagag | 960 |
| gttgcggtga | gccgagatca | cgccattttg | cacttcagcc | taggcaacaa gagcgaaact | 1020 |
| ccgtctcaaa | aaaaaaaaa | aaaaaaaat | tcctattgga | gactagtccc tccgtaaaca | 1080 |
| ctacgattcc | catccaccct | tgccttccag | tgctcctttg | ttactcattg tttatagtta | 1140 |
| atcttcagct | tctctcaact | gagcccattt | catcattatt | cagaactgct tgggccgggc | 1200 |
| gcagtggctt | atggcctgta | atcatcttag | gaggccaagg | tgggaggatc gcttgaccct | 1260 |
| aggagttcaa | gactagcctg | gcaacatag | tgaaaccttg | tctctacaaa aagaaaatta | 1320 |
| aaaattagtt | gggcatggtg | gtgcgcacct | gtagtcccag | ctacaggagg ctgaggtgag | 1380 |
| aggatggctt | gagcccagga | ggtcgaggct | gcagtgagcc | atgttcttat tgcactccag | 1440 |
| cctgagtggc | agagcagcaa | agtgagggac | acactgtctc | taaaaacaaa acaaacaaac | 1500 |
| aaaaaaaaa | caaaaataaa | aaaactcttt | ggatttctcc | tatcctaaaa aagggaaact | 1560 |
| cttttgacta | tcccccatcc | cattaattca | tttaacaggt | atctattgtg tacagtttac | 1620 |
| ctggcactga | ctttggacac | acaccaatca | acaagagaat | cagtccttgc actcaagtcg | 1680 |
| ttttttacag | tcaaattcag | gaagtacaca | ctgatgaaa | gaatcaaagt aatgtaaaat | 1740 |
| tacattaggt | aagagctaca | aggcagaaat | atgtgatagg | ataagatgag gggacctgat | 1800 |
| ttggacattt | cagtcaagac | ttgaaaaatg | ataaggtgtt | aggtaaaagc ataaagagt | 1860 |
| ccaaacagag | gaaatggatt | gtgtgaggcc | ccaaggtggg | cagacacact tgaggtgttt | 1920 |
| aagcaactaa | attcagtcaa | ccttggctag | agcatagtga | ggggatgagg cggatggtgc | 1980 |
| ccggatcact | ggacctgcaa | ggctgtagta | agaggactgc | cttctaagag caagggtgtg | 2040 |

```
gcagccaaat ccctccaatg gcctataagg tactttgtga ccctcctctc cccacctcat    2100
ctggtttact tctctgacct cttctaccac tcagtcccat ctcattccat tctaaccaca    2160
ttgacctact tactgtacca cagacatacc aggcaccctc cttggggcct ttgcactcac    2220
ttagaatgct ttgggtctac cttgaccaca gtctttaaaa ttgcaacatt aaaccccacc    2280
ttggcactct ttttttttccc ctcttggtct aattttttgct ttttatgcta atatttatca   2340
cctaacatct tatggaattt acttatgttc attattcctt ttctgtcccc attagaatat    2400
aagctccctg agggcaggaa cttttgatgt tttatttact gaagtatgcc aagtgcctaa    2460
aactgcttgg cacatattag ggggctctat aaatatttgc tcaatctttt tttttctttta  2520 agagacaagg tcttgctgag cccagggtgg agtgcagtgg cacaatcata gctcactgca    2580
gcctcgacct tctgggctca agctgttctt cacttcagcc tccagagtag caggattaca    2640
gtgttgagcc accacaacca gcttgctcaa gaatttaatg acccatagta aaggcctaca    2700
gtatttaaaa aagaaagaaa aaggaaaaaa ggaaggaagg aaagagggag ggagaaaaaa    2760
agagaaaaga aagaaaataa aagaatataa tggggtgtca ccaggcgccg tggctcatgc    2820
ctgtatccca gcactttggg aggccgaggc gggttgattg cttgagctct ggaggtggag    2880
actagcctgg gcaacatggt gaaaccctgt ctctaacaaa aatacaaaaa ttagctggat    2940
gtggtggtgg tgtgcgcctg tggtcccagc tgcttggagt tggggtgggg tattggggtg    3000
ggaggattgc ttgagccgag gaagcagagg ttgcagtgag ccaagatcac accactgcac    3060
tccagcctgg gtgacagagt gagaccccat cccaaaaaaa aaaaaagaa tgggaaacca    3120 ttgaaggtta taaggaagga agtgacgtga tctggaaaag attcctttgc tctttggaga    3180
atagattgta gaatgaatgt ggaagtaagc aggtttggtg aaggaagttt ggctatgaag    3240
ggaaggaggg tgggatttga ttgtgttacg agccaagggg aaaatctttc cctttgccct    3300
ctgaagatct gctgaaaaat cagctcacaa aaggcaggtt aactggagaa aaggcataca    3360
aatttattaa catgcacatt gggagaacca taaagtgatt acccatctcc ctacagagtt    3420
cgtgagttta taccatctc ggcaaaacag attatgggag gggtgtctca cgtgtgtcca    3480
tgtgaagaga ccaccaaaca ggctttgtct gagcaacaag gctgtttatt tcacctgggt    3540
gcagacaggc tgagtctgaa aaaaggagt cagcaaaggg tggtggaatt atcattagtt    3600
cttataggtt ttgggatagg cattggagtt aagagcaatg ttttgggggc aggggtggga    3660
tctcacaaag tacattctca agggtgggga gattataaaa aaccttctta agggtggggg    3720
ggagattacc aagtacattg atcagttagc gtggggcaga aacaaatcac agtggtggaa    3780
tgtgatcagt taaggctatt ttcacttctt ttgtagatct tcagttgctt caggccatct    3840
ggatgtataa gtgcaggtta ctgaggatat gatggcttag cttgggctca gaggcctgac    3900
aaggggtaga agagaaattc tgttttttctg tttttgtaga gacggggtct tgctatgttg    3960
caagcctaat ctcgaactcc tgggctcaag taatcctcct gccttggcct cccaaagtgc    4020
tgggattaca ggcctgagcc agcatgtcca gctctatttg ttttttaaata aaccgaactt    4080 tggccagaag gagattctgt tgaagggcaa taaggattaa ctagagagaa tggaatgggg    4140
acagaggttg acttgttaat agttctcttt ggaatttgag tgatcctgag gtacacaata    4200
cctgtgaaag ggtttgttca ggtgtggtta catgttagtc ttattgggag gggaagaaaa    4260
aacaagtatt cttttagtg agtttggact ttaggcagat aaaagagttcc agagaacaac    4320 tttatcctgg ctttgggaga gtctggggtg gaaggatcag agagaccttg cggcttcttg    4380
```

```
agttcagcat gtcagagggc catattttgg ggtattggtt tcttttcttt tctttttttt    4440
tgagacagag tcttgctctg tctttgttgc ccaggctgtg cagtggcatg atctcagctc    4500
actgcaagct ctgcctcctg ggttcaagcg agcacgtctg gctaattttt ttggattttt    4560
agtagagatg gggtttcgcc atgttggcca ggctggtctc gaactcctgg cctcaagtga    4620
tctgcctgcc ttagcctccc gcagtgttgg gattacaggc atgagccacc gtgcctggcc    4680
tggggtatta gtttctgagt tccaacagtt agacgggatt ggaggagcag gaccctgaag    4740
aggaggaggg taagacagtg caaatggagg tagatttgaa gttggttttt tttttctga     4800 aggaggaggc aagctctttt gatgaaaatg aggtggtaaa gtcaaaggtt tggggggaga    4860
gtttgataca gaggcttagc agggactgca ttttatcaca gtataagaat gctggtcgtg    4920
gatttgaaag aacaagtcgc ttaatctcca taaacctcaa tttccttata actaaggtgg    4980
aggtgatact agtacatacc tcatagagtc accaggagat tgagagatcc ggtaaagctc    5040
ttcatggggt ctgacataga gtaggcactc acaaaatatc aactaatttt agctgttaga    5100
gaaaaggcgg ccattataac agttagggag cagtgaaaat caaccaggca cattttctca    5160
ttgttgatgt tcagccacct atggtttact agattaggaa taaaaatagc taatctctgt    5220
tctcccactg atttgccatc tgttctcaga cagatctttt gtccctctga tccttggttt    5280
cttctaggat aaaatgaagg ttttggactt aatgactact acaggctgtt tcagtgtaac    5340
catgctacat ctctaagagg cagagaaacc gcctaccccc attctcccag acacacctaa    5400 acaacccta tccacacaca cagtcacagt aagcatcaga gatacacaaa tgctcccaaa     5460
caggaggctt tcatccttga cccatcccag ccctggcctc acagtctttg catgtctcca    5520
gggctgtaac gccggccccc ttgaggccac ttgctcagct atactagttg tatctcagtg    5580
ctgcagccag ccaagagtaa acccgtgagc atcttgagag tgcttgagag aagctggacc    5640
ccatgtgaat ggtggatgag agggagatag ctatcaccct tggaaggcct caaaatttgg    5700
cctcattgtg actgactgct ttggctgggt cttttttgttt caggccatca tgaggaagcc    5760
acgagcagcc gtgggaagtg gtcacaggaa gcaggcagcc agccaggaag ggaggcagaa    5820
gcatgctaag aacaacagtc aggccaagcc ttctgcctgt gatggtaagg aactaggttg    5880
tggcccaagg ctcattggcc atgaaaggca gattcaggct gggaagggat tgtgatacgt    5940
atcaagacat taagagactt actaagggcc aggtgcggtg gctcacacct gtaatcccag    6000
cactttggga ggccgaggca ggtggatccc ttgagcccag gagtttgaga ccagcttggg    6060
taacatggcg aaatcccctc tctatgctcg cgtggtggtg agcgtctgta gtcccagcta    6120
ctcgggaagc tgaggtgaca ggatcgcttg agcctggaag gcagaagttg cactgagtca    6180
agataatgca actgcatttc agtctgggca acagagccag actcttgtct caaaacaaaa    6240
gagactcact gagggtgtaa ttctgactgt attgctgtgt gacattggga caattgctct    6300
gaatggctgc tttcttacca gtaaaatgga gcagtagttc agcatttcct ccctcatgtg    6360
gctttcatgg gaccaaatga gtttatgagc ctgaaagtgt tttgtgaata ggaaggtcct    6420
gcaccagtat acattctagc tggctaaaac tattaggttt tcattatggc tcagagacaa    6480
gccagtagta ccaccctgag aaaattaagg ccagaaactt agccacagct acacacaatt    6540
acataactct ggtctgactc cagctccaaa gcttaagggg gttagttggg ggaagcccta    6600
agtgggagca tactgccaca ggctgctgtg tcccaagacc ctgatgcaca gcctgtgcag    6660
ggatgattgc tgagtgtcct ggggccccag caggcctggc caggcagccg gaagaggtgg    6720
tattgcaggc ctctgtctcc tcataccatc tattcagaga cgtagctgaa gtcacagcct    6780
```

```
tccgagggag cctgctaagc tggtacgacc aagagaaacg ggacctacca tggagaagac    6840
gggtaggcag gcgaggagca gggacagtgg gtgggaggca ggcacccagc cccctccacc    6900
ctaactcctc atctggggtt gcattgacag gcagaagatg agatggacct ggacaggcgg    6960
gcatatgctg gtcagtacat ctcctgagag cagggccact ttgcctcgag gcccttgggt    7020
ctggggggctg tgggccaggt aggggcaggt cagcagtgtc ctcatgccaa cccctttccc    7080
ccaatgtggg tctcagaggt catgctgcag cagacccagg ttgccactgt gatcaactac    7140
tataccggat ggatgcaggt gactccaggg aggaaggga agggtcatgg gtcagacccc       7200
agatgagagc ctctactttg gggtgggtgt agagaaggct tcctctacca ccttcaccct    7260
tgaccttgtc tctttctgcc tgcctgtggc tatagaagtg gcctacactg caggacctgg    7320
ccagtgcttc cctggaggtg agagccaccc tagggtaggg gaaataggaa caatagaggg    7380
actgacgggt gatctctttg acctctgatc ctacccacag gaggtgaatc aactctgggc    7440
tggcctgggc tactattctc gtggccggcg gctgcaggag ggagctcgga aggtaagggg    7500
atggcaggag ggtaggaacc caggagtctt gggtgtctta taatcttgag tcttgcactc    7560
caatcaggtg gtagaggagc tagggggcca catgccacgt acagcagaga ccctgcagca    7620
gctcctgcct ggcgtggggc gctacacagc tggggccatt gcctctatcg cctttggcca    7680
ggtgatctca cagcccaccc ccactttgtg cgtgcccagc ctccttcctc ccagcccagg    7740
ctaactcttt ggcccctctg tgccaggcaa ccggtgtggt ggatggcaac gtagcacggg    7800
tgctgtgccg tgtccgagcc attggtgctg atcccagcag cacccttgtt tcccagcagc    7860
tctggtagga tgttggggta acaagggtgc ttcaggggtg tctgcaaagg agctctgctt    7920
cacagcagtg ttcccttctt ttaggggtct agcccagca ctggtggacc cagcccggcc    7980
aggagatttc aaccaagcag ccatggagct aggggccaca gtgtgtaccc cacagcgccc    8040
actgtgcagc cagtgccctg tggagagcct gtgccgggca cgccagagag taagcctact    8100
ggggaagggg cagtgagaag tcctaaggag tgactctgcc ctatgacact caaccctgtg    8160
cctctcaggt ggagcaggaa cagctcttag cctcagggag cctgtcgggc agtcctgacg    8220
tggaggagtg tggtgagcac caaacctagc ccccacccca acccttcctg gcccagtcag    8280
aagccccatt ccagttcttc ctctaacctg agtaagattc tgcagaaccc ggccaaagcc    8340
cactctctag gttggcccct aaagccctct tggcttgagt agggttcggg gatctccgtt    8400
cccagctccc aacactggac agtgccacct gtgcctgcct ccctcggagc cctgggacca    8460
gaccctggga gtggtcaact tccccagaaa ggccagccgc aagcccccca gggaggagag    8520
ctctgccacc tgtgttctgg aacagcctgg ggccttggg gcccaaattc tgctggtgca    8580
gaggcccaac tcaggtacct ggatactggg cgtggagggc agtggcatga gtaacaagag    8640
agaatggagg gaatcggcag ctgaggcctg acccctgcct ggctgccctc cctctcaggt    8700
ctgctggcag gactgtggga gttcccgtcc gtgacctggg agccctcaga gcagcttcag    8760
cgcaaggccc tgctgcagga actacagcgt tgggctgggc cctcccagc cacgcacctc    8820
cggcaccttg gggaggtaag tgagcagcgg aatagccaag gatgttggct tttgaggcta    8880
tatccacagg cctatttgaa ccccttgacc cttcctccag gttgtccaca ccttctctca    8940
catcaagctg acatatcaag tatatgggct ggccttggaa gggcagaccc cagtgaccac    9000
cgtaccacca ggtgctcgct ggctgacgca ggaggaattt cacaccgcag ctgtttccac    9060
cgccatgaaa aaggcactac ctttgttgtc tttgttgtac ttccttgtgt ttcctacatg    9120
```

```
ttctacatga atatattact gtgtaaacag gaaaaaaagc attttttttt gagacggaga    9180
atcgctctgt tgcccaggct ggagtgcaat ggcgctatct cggttgactg caacctccat    9240
ctcccgggtt caagtgattc tcctgcctca gcttcctgag tagctcggat tacaggcgcc    9300
cgccaccatg cctggctaat ttttgtattt ttagtagaga tgaggtttca ccatgctggc    9360
caggctggtc tccaactctt gacctcaagt gatccgcccg cctcagcctc ccagaatgct    9420
gggattacag gtgtgagcta ccacacccag ccatgatttt ttgtattttt agagatgggg    9480
tttcaccatg ttggccaggc tggtctcaaa ctcctggcct caagtgatcc acccgacttg    9540
gcctcccaaa atgctgggat tataggcgtg agccaccatg cctggccaaa aaagcatatt    9600
ttaaacaaaa gtactgggac atgaagttaa gggcagaaca ccggtttatc tcttttgcaa    9660
aaagtgccag ccctcacctc cctgtcttct tgtctaggtt ttccgtgtgt atcagggcca    9720
acagccaggg acctgtatgg taagtctcct aggcctctcc caaccgtgtc tccccaggcc    9780
tgagtccata ggttttttagt cagttaacta acgaatgtct gggtgaacat tctccactcc    9840
aggcttcact ggagggagga atagttcttg acctggagac cttccattgt ggggtgcagg    9900
gtagagggaa aggaaaaaaa tgatgaggac tctccagtgt cacaggtgtg tgaaatgcct    9960
gtactgagtt ttgtgggata tgaattgtgg agccatcagt tctttttttt tttttttttt   10020
tttttttgaga cagtctcact gtcacccaag ctagagtgca gtggcccgat ctcggctcac   10080
tgcaatctcc cacaactgga ttaaagcgat tctcctgcct cagtctccca gtagctggg   10140
attacaggtg cctgctacca cacccaacta attttttgtat ttttagtaga cagggtttt   10200
caccatgttg actaggctgg tctcgaactc ctgacctcaa gtgatctgcc catcttggcc   10260
tcccaaagtg ctgggattac aggcgtgagc caccacaccc atccatggga gctatcagtt   10320
ctaattggga gacggatcag gaaaggctgt ttggaggaag cagctggtaa tcttcgtcct   10380
agaaatgaat cctttttcttc aggttttggga ggggaatcaa ccgtagcgat gttctttcca   10440
gtcccaagag tagtgtgagc aaaggtggag cccagtgcag gctgcagtgc tcaaggagct   10500
gtgagcagtt ggtttagctg gaaaggtcag cagggcctgc tgggtcagtc agggtgtgag   10560
ccctaggctg ctgactcatt ttaggtggag gagagaggag tcagatttgc attttagga   10620
caattcgatt ccctcaggca gcctttgga gggttgattg atggggcaga tacttgaggc   10680
aggatgaaag ctctacagca ttccaggcta agcctagcta gatcagtaga gtcggggaaa   10740
gggagagagg acaaggagag gattctctgc tcccctccc ccaactacaa ggcctccctc   10800
cttccattt ttcacagggt tccaaaaggt cccaggtgtc ctctccgtgc agtcggaaaa   10860
agccccgcat gggccagcaa gtcctggata atttctttcg gtctcacatc tccactgatg   10920
cacacagcct caacagtgca gcccagtga                                      10949
```

<210> SEQ ID NO 2
<211> LENGTH: 10949
<212> TYPE: DNA
<213> ORGANISM: Homo sapiens

<400> SEQUENCE: 2

```
atgacaccgc tcgtctcccg cctgagtcgt ctgtgggtac gctggacttg cggtccgtct     60
cctggcgcgg ttcaggcagt cggggatggg gcggggtctc gccgtcgggt cgccgatggg    120
tcgaacttcc gttcagacgt cccgggtccg gcgcggggaa ggcagcctgg cgcgcgctaa    180
ttgcctattg gctgtgctg ccggctcgca gcccgggtgg acccgagcca cgccccctgg    240
agtgcgccgg aaagccgggc gcgctagagc tcgcgggagg taatctttct ctcctgctct    300
```

-continued

```
cgcggcggga acgcggggcc tccgtgttct gctgtcttca tcagcgtggg ccgcgggtag      360
cgggtagtgg ggtggctggg tttgggcttt ccagagaagg tgacgctgcc tgagctgagc      420
ttaaagcacg cccaggagtt agactaggag agggtcgtgt gggggaaaga agggcgttct      480
gggcatcggt aaattcccag agaggatgga gagctcagtg atctccagaa agtgaaagag      540
gcggggagtg ggccatcgga ggaggctgcc cagggtgtaa gagcgaccga ttggtaggga      600
agcttttgta ataatccaat caagtgataa tgtgaacttg aattaaggct ggcagtatgg      660
atggcgagga agggacaaat tgtgaagcag ctaggcggta tagtcgacct agagggtgat      720
tgaatttgaa agaggttcct aggccgggcg cggtggctca cgcctgtaat cccagcactt      780
tgggaggccg aggcgggcgg attacctgag gtccggagtt caaaaccagc ctggccaaca      840
tggtgaaacc ccgtctctac taaaagtaca aaaaaaatta gctgggtatg gtgcgggcgc      900
ctgtaatccc actacttggg aggctgaggc aggagaatcg cttgaacctg ggaggcagag      960
gttgcggtga gccgagatca cgccattttg cacttcagcc taggcaacaa gagcgaaact     1020
ccgtctcaaa aaaaaaaaaa aaaaaaaaat tcctattgga gactagtccc tccgtaaaca     1080
ctacgattcc catccaccct ctgccttcag tgctcctttg ttactcattg tttatagtta     1140
atcttcagct tctctcaact gagcccattt catcattatt cagaactgct tgggccgggc     1200
gcagtggctt atggcctgta atcatcttag gaggccaagg tgggaggatc gcttgaccct     1260
aggagttcaa gactagcctg gcaacatag tgaaaccttg tctctacaaa agaaaatta      1320 aaaattagtt gggcatggtg gtgcgcacct gtagtcccag ctacaggagg ctgaggtgag     1380
aggatggctt gagcccagga ggtcgaggct gcagtgagcc atgttcttat tgcactccag     1440
cctgagtggc agagcagcaa agtgagggac acactgtctc taaaaacaaa acaaacaaac     1500
aaaaaaaaaa caaaaataaa aaactctttt ggatttctcc tatcctaaaa aagggaaact     1560
cttttgacta tcccccatcc cattaattca tttaacaggt atctattgtg tacagtttac     1620
ctggcactga ctttggacac acaccaatca acaagagaat cagtccttgc actcaagtcg     1680
ttttttacag tcaaattcag gaagtacaca ctgatgaaaa gaatcaaagt aatgtaaaat     1740
tacattaggt aagagctaca aggcagaaat atgtgatagg ataagatgag gggacctgat     1800
ttggacattt cagtcaagac ttgaaaaatg ataaggtgtt aggtaaaagc ataaagagt      1860 ccaaacagag gaaatggatt gtgtgaggcc ccaaggtggg cagacacact tgaggtgttt     1920
aagcaactaa attcagtcaa ccttggctag agcatagtga ggggatgagg cggatggtgc     1980
ccggatcact ggacctgcaa ggctgtagta agaggactgc cttctaagag caagggtgtg     2040
gcagccaaat ccctccaatg gcctataagg tactttgtga ccctcctctc cccacctcat     2100
ctggtttact tctctgacct cttctaccac tcagtcccat ctcattccat tctaaccaca     2160
ttgacctact tactgtacca cagacatacc aggcaccctc cttggggcct ttgcactcac     2220
ttagaatgct ttgggtctac cttgaccaca gtctttaaaa ttgcaacatt aaaccccacc     2280
ttggcactct ttttttttccc ctcttggtct aattttgct ttttatgcta atatttatca     2340
cctaacatct tatggaattt acttatgttc attattcctt ttctgtcccc attagaatat     2400
aagctccctg agggcaggaa cttttgatgt tttatttact gaagtatgcc aagtgcctaa     2460
aactgcttgg cacatattag ggggctctat aaatatttgc tcaatctttt tttttcttta     2520
agagacaagg tcttgctgag cccagggtgg agtgcagtgg cacaatcata gctcactgca     2580
gcctcgacct tctgggctca agctgttctt cacttcagcc tccagagtag caggattaca     2640
```

```
gtgttgagcc accacaacca gcttgctcaa gaatttaatg acccatagta aaggcctaca      2700
gtatttaaaa aagaaagaaa aaggaaaaaa ggaaggaagg aaagagggag ggagaaaaaa      2760
agagaaaaga aagaaaataa aagaatataa tggggtgtca ccaggcgccg tggctcatgc      2820
ctgtatccca gcactttggg aggccgaggc gggttgattg cttgagctct ggaggtggag      2880
actagcctgg gcaacatggt gaaaccctgt ctctaacaaa aatacaaaaa ttagctggat      2940
gtggtggtgg tgtgcgcctg tggtcccagc tgcttggagt tggggtgggg tattggggtg      3000
ggaggattgc ttgagccgag gaagcagagg ttgcagtgag ccaagatcac accactgcac      3060
tccagcctgg gtgacagagt gagacccat cccaaaaaaa aaaaaagaa tgggaaacca       3120 ttgaaggtta taaggaagga agtgacgtga tctggaaaag attcctttgc tctttggaga      3180
atagattgta gaatgaatgt ggaagtaagc aggtttggtg aaggaagttt ggctatgaag      3240
ggaaggaggg tgggatttga ttgtgttacg agccaagggg aaaatctttc cctttgccct      3300
ctgaagatct gctgaaaaat cagctcacaa aaggcaggtt aactggagaa aaggcataca      3360
aatttattaa catgcacatt gggagaacca taaagtgatt acccatctcc ctacagagtt      3420
cgtgagttta taccatctc ggcaaaacag attatgggag gggtgtctca cgtgtgtcca       3480
tgtgaagaga ccaccaaaca ggctttgtct gagcaacaag gctgtttatt tcacctgggt      3540
gcagacaggc tgagtctgaa aaaaaggagt cagcaaaggg tggtggaatt atcattagtt      3600
cttataggtt ttgggatagg cattggagtt aagagcaatg ttttggggc agggggtgga       3660 tctcacaaag tacattctca agggtgggga gattataaaa aaccttctta agggtggggg      3720
ggagattacc aagtacattg atcagttagc gtggggcaga aacaaatcac agtggtggaa      3780
tgtgatcagt taaggctatt ttcacttctt ttgtagatct tcagttgctt caggccatct      3840
ggatgtataa gtgcaggtta ctgaggatat gatggcttag cttgggctca gaggcctgac      3900
aaggggtaga agagaaattc tgttttttctg tttttgtaga gacggggtct tgctatgttg       3960
caagcctaat ctcgaactcc tgggctcaag taatcctcct gccttggcct cccaaagtgc      4020
tgggattaca ggcctgagcc agcatgtcca gctctatttg ttttaaata aaccgaactt       4080 tggccagaag gagattctgt tgaagggcaa taaaggatta ctagagagaa tggaatgggg      4140
acagaggttg acttgttaat agttctcttt ggaatttgag tgatcctgag gtacacaata      4200
cctgtgaaag ggtttgttca ggtgtggtta catgttagtc ttattgggag gggaagaaaa      4260
aacaagtatt ctttttagtg agtttggact ttaggcagat aaaagagttcc agagaacaac      4320 tttatcctgg ctttgggaga gtctggggtg gaaggatcag agagaccttg cggcttcttg      4380
agttcagcat gtcagagggc catattttgg ggtattggtt tcttttctttt tcttttttttt     4440 tgagacagag tcttgctctg tctttgttgc ccaggctgtg cagtggcatg atctcagctc      4500
actgcaagct ctgcctcctg ggttcaagcg agcacgtctg gctaattttt ttggattttt      4560
agtagagatg gggtttcgcc atgttggcca ggctggtctc gaactcctgg cctcaagtga      4620
tctgcctgcc ttagcctccc gcagtgttgg gattacaggc atgagccacc gtgcctggcc      4680
tggggtatta gttctgagt tccaacagtt agacggatt ggaggagcag gaccctgaag        4740
aggaggaggg taagacagtg caaatggagg tagatttgaa gttggttttt ttttttctga      4800
aggaggaggc aagctctttt gatgaaaatg aggtggtaaa gtcaaaggtt tgggggagga      4860
gtttgataca gaggcttagc agggactgca ttttatcaca gtataagaat gctggtcgtg      4920
gatttgaaag aacaagtcgc ttaatctcca taaacctcaa tttccttata actaaggtgg      4980
aggtgatact agtacatacc tcatagagtc accaggagat tgagagatcc ggtaaagctc      5040
```

```
ttcatggggt ctgacataga gtaggcactc acaaaatatc aactaatttt agctgttaga    5100
gaaaaggcgg ccattataac agttagggag cagtgaaaat caaccaggca cattttctca    5160
ttgttgatgg tcagccacct atggtttact agattaggaa taaaaatagc taatctctgt    5220
tctcccactg atttgccatc tgttctcaga cagatctttt gtccctctga tccttggttt    5280
cttctaggat aaaatgaagg ttttggactt aatgactact acaggctgtt tcagtgtaac    5340
catgctacat ctctaagagg cagagaaacc gcctaccccc attctcccag acacacctaa    5400 acaacccta tccacacaca cagtcacagt aagcatcaga gatacacaaa tgctcccaaa    5460
caggaggctt tcatccttga cccatcccag ccctggcctc acagtctttg catgtctcca    5520
gggctgtaac gccggccccc ttgaggccac ttgctcagct atactagttg tatctcagtg    5580
ctgcagccag ccaagagtaa acccgtgagc atcttgagag tgcttgagag aagctggacc    5640
ccatgtgaat ggtggatgag agggagatag ctatcaccct tggaaggcct caaaatttgg    5700
cctcattgtg actgactgct ttggctgggt cttttttgttt caggccatca tgaggaagcc    5760
acgagcagcc gtgggaagtg gtcacaggaa gcaggcagcc agccaggaag ggaggcagaa    5820
gcatgctaag aacaacagtc aggccaagcc ttctgcctgt gatggtaagg aactaggttg    5880
tggcccaagg ctcattggcc atgaaaggca gattcaggct gggaagggat tgtgatacgt    5940
atcaagacat taagagactt actaagggcc aggtgcggtg gctcacacct gtaatcccag    6000
cactttggga ggccgaggca ggtggatccc ttgagcccag gagtttgaga ccagcttggg    6060
taacatggcg aaatcccctc tctatgctcg cgtggtggtg agcgtctgta gtcccagcta    6120
ctcgggaagc tgaggtgaca ggatcgcttg agcctggaag gcagaagttg cactgagtca    6180
agataatgca actgcatttc agtctgggca acagagccag actcttgtct caaaacaaaa    6240
gagactcact gagggtgtaa ttctgactgt attgctgtgt gacattggga caattgctct    6300
gaatggctgc tttcttacca gtaaaatgga gcagtagttc agcatttcct ccctcatgtg    6360
gctttcatgg gaccaaatga gtttatgagc ctgaaagtgt tttgtgaata ggaaggtcct    6420
gcaccagtat acattctagc tggctaaaac tattaggttt tcattatggc tcagagacaa    6480
gccagtagta ccaccctgag aaaattaagg ccagaaactt agccacagct acacacaatt    6540
acataactct ggtctgactc cagctccaaa gcttaagggg gttagttggg ggaagcccta    6600
agtgggagca tactgccaca ggctgctgtg tcccaagacc ctgatgcaca gcctgtgcag    6660
ggatgattgc tgagtgtcct ggggccccag caggcctggc caggcagccg gaagaggtgg    6720
tattgcaggc ctctgtctcc tcataccatc tattcagaga cgtagctgaa gtcacagcct    6780 tccgaggag cctgctaagc tggtacgacc aagagaaacg ggacctacca tggagaagac    6840
gggtaggcag gcgaggagca gggacagtgg gtgggaggca ggcacccagc cccctccacc    6900
ctaactcctc atctggggtt gcattgacag gcagaagatg agatggacct ggacaggcgg    6960
gcatatgctg gtcagtacat ctcctgagag cagggccact ttgcctcgag gcccttgggt    7020 ctggggctg tgggcaggt aggggcaggt cagcagtgtc ctcatgccaa ccccttccc    7080 ccagtgtggg tctcagaggt catgctgcag cagacccagg ttgccactgt gatcaactac    7140
tataccggat ggatgcaggt gactccaggg gaggaaggga agggtcatgg gtcagaccc    7200 agatgagagc ctctactttg gggtgggtgt agagaaggct tcctctacca ccttcaccct    7260
tgaccttgtc tctttctgcc tgcctgtggc tatagaagtg gcctacactg caggacctgg    7320
ccagtgcttc cctggaggtg agagccaccc tagggtaggg gaaataggaa caatagaggg    7380
```

```
actgacgggt gatctctttg acctctgatc ctacccacag gaggtgaatc aactctgggc   7440
tggcctgggc tactattctc gtggccggcg gctgcaggag ggagctcgga aggtaagggg   7500
atggcaggag ggtaggaacc caggagtctt gggtgtctta taatcttgag tcttgcactc   7560
caatcaggtg gtagaggagc tagggggcca catgccacgt acagcagaga ccctgcagca   7620
gctcctgcct ggcgtggggc gctacacagc tggggccatt gcctctatcg cctttggcca   7680
ggtgatctca cagcccaccc ccactttgtg cgtgcccagc ctccttcctc ccagcccagg   7740
ctaactcttt ggccctctg tgccaggcaa ccggtgtggt ggatggcaac gtagcacggg   7800
tgctgtgccg tgtccgagcc attggtgctg atcccagcag cacccttgtt cccagcagc   7860 tctggtagga tgttggggta caagggtgc ttcaggggtg tctgcaaagg agctctgctt   7920
cacagcagtg ttcccttctt ttaggggtct agcccagcag ctggtggacc cagcccggcc   7980
aggagatttc aaccaagcag ccatggagct aggggccaca gtgtgtaccc cacagcgccc   8040
actgtgcagc cagtgccctg tggagagcct gtgccgggca cgccagagag tcagcctact   8100
ggggaagggg cagtgagaag tcctaaggag tgactctgcc ctatgacact caaccctgtg   8160
cctctcaggt ggagcaggaa cagctcttag cctcagggag cctgtcgggc agtcctgacg   8220
tggaggagtg tggtgagcac caaacctagc ccccacccca accttcctg gcccagtcag   8280 aagccccatt ccagttcttc ctctaacctg agtaagattc tgcagaaccc ggccaaagcc   8340
cactctctag gttggcccct aaagccctct tggcttgagt agggttcggg gatctccgtt   8400
cccagctccc aacactggac agtgccacct gtgcctgcct ccctcggagc cctgggacca   8460
gaccctggga gtggtcaact tccccagaaa ggccagccgc aagcccccca gggaggagag   8520
ctctgccacc tgtgttctgg aacagcctgg ggcccttggg gcccaaattc tgctggtgca   8580
gaggcccaac tcaggtacct ggatactggg cgtggagggc agtggcatga gtaacaagag   8640
agaatggagg gaatcggcag ctgaggcctg acccctgcct ggctgccctc cctctcaggt   8700
ctgctggcag gactgtggga gttcccgtcc gtgacctggg agccctcaga gcagcttcag   8760
cgcaaggccc tgctgcagga actacagcgt tgggctgggc cctcccagc cacgcacctc   8820 cggcaccttg gggaggtaag tgagcagcgg aatagccaag gatgttggct tttgaggcta   8880
tatccacagg cctatttgaa ccccttgacc cttcctccag gttgtccaca ccttctctca   8940
catcaagctg acatatcaag tatatgggct ggccttggaa gggcagaccc cagtgaccac   9000
cgtaccacca ggtgctcgct ggctgacgca ggaggaattt cacaccgcag ctgtttccac   9060
cgccatgaaa aaggcactac ctttgttgtc tttgttgtac ttccttgtgt ttcctacatg   9120
ttctacatga atatattact gtgtaaacag gaaaaaaagc attttttttt gagacggaga   9180
atcgctctgt tgcccaggct ggagtgcaat ggcgctatct cggttgactg caacctccat   9240
ctcccgggtt caagtgattc tcctgcctca gcttcctgag tagctcggat tacaggcgcc   9300
cgccaccatg cctggctaat ttttgtattt ttagtagaga tgaggtttca ccatgctggc   9360
caggctggtc tccaactctt gacctcaagt gatccgcccg cctcagcctc ccagaatgct   9420
gggattacag gtgtgagcta ccacacccag ccatgatttt ttgtattttt agagatgggg   9480
tttcaccatg ttggccaggc tggtctcaaa ctcctggcct caagtgatcc acccgacttg   9540
gcctcccaaa atgctgggat tataggcgtg agcaccatg cctggccaaa aaagcatatt   9600
ttaaacaaaa gtactgggac atgaagttaa gggcagaaca ccggtttatc tcttttgcaa   9660
aaagtgccag ccctcacctc cctgtcttct tgtctaggtt ttccgtgtgt atcagggcca   9720
acagccaggg acctgtatgg taagtctcct aggcctctcc caaccgtgtc tccccaggcc   9780
```

-continued

```
tgagtccata ggttttagt cagttaacta acgaatgtct gggtgaacat tctccactcc      9840
aggcttcact ggagggagga atagttcttg acctggagac cttccattgt ggggtgcagg      9900
gtagagggaa aggaaaaaaa tgatgaggac tctccagtgt cacaggtgtg tgaaatgcct      9960
gtactgagtt ttgtgggata tgaattgtgg agccatcagt tctttttttt tttttttttt     10020
tttttgaga cagtctcact gtcacccaag ctagagtgca gtggcccgat ctcggctcac      10080
tgcaatctcc cacaactgga ttaaagcgat tctcctgcct cagtctccca agtagctggg     10140
attacaggtg cctgctacca cacccaacta attttgtat ttttagtaga cagggttt       10200
caccatgttg actaggctgg tctcgaactc ctgacctcaa gtgatctgcc catcttggcc     10260
tcccaaagtg ctgggattac aggcgtgagc caccacaccc atccatggga gctatcagtt     10320
ctaattggga gacggatcag gaaaggctgt ttggaggaag cagctggtaa tcttcgtcct     10380
agaaatgaat ccttttcttc aggtttggga ggggaatcaa ccgtagcgat gttctttcca     10440
gtcccaagag tagtgtgagc aaaggtggag cccagtgcag gctgcagtgc tcaaggagct     10500
gtgagcagtt ggtttagctg gaaaggtcag cagggcctgc tgggtcagtc agggtgtgag     10560
ccctaggctg ctgactcatt ttaggtggag gagagaggag tcagatttgc atttttagga    10620
caattcgatt ccctcaggca gccttttgga gggttgattg atggggcaga tacttgaggc     10680
aggatgaaag ctctacagca ttccaggcta agcctagcta gatcagtaga gtcggggaaa     10740
gggagagagg acaaggagag gattctctgc tccccctccc ccaactacaa ggcctccctc     10800
cttccatttt ttcacagggt tccaaaaggt cccaggtgtc ctctccgtgc agtcggaaaa     10860
agccccgcat gggccagcaa gtcctggata atttctttcg gtctcacatc tccactgatg     10920
cacacagcct caacagtgca gcccagtga                                       10949
```

<210> SEQ ID NO 3
<211> LENGTH: 1608
<212> TYPE: DNA
<213> ORGANISM: Homo sapiens
<220> FEATURE:
<221> NAME/KEY: exon
<222> LOCATION: (1)..(1608)

<400> SEQUENCE: 3

```
atg aca ccg ctc gtc tcc cgc ctg agt cgt ctg tgg gcc atc atg agg        48
Met Thr Pro Leu Val Ser Arg Leu Ser Arg Leu Trp Ala Ile Met Arg
1               5                   10                  15 aag cca cga gca gcc gtg gga agt ggt cac agg aag cag gca gcc agc        96
Lys Pro Arg Ala Ala Val Gly Ser Gly His Arg Lys Gln Ala Ala Ser
                20                  25                  30 cag gaa ggg agg cag aag cat gct aag aac aac agt cag gcc aag cct       144
Gln Glu Gly Arg Gln Lys His Ala Lys Asn Asn Ser Gln Ala Lys Pro
            35                  40                  45 tct gcc tgt gat ggc ctg gcc agg cag ccg gaa gag gtg gta ttg cag       192
Ser Ala Cys Asp Gly Leu Ala Arg Gln Pro Glu Glu Val Val Leu Gln
        50                  55                  60 gcc tct gtc tcc tca tac cat cta ttc aga gac gta gct gaa gtc aca       240
Ala Ser Val Ser Ser Tyr His Leu Phe Arg Asp Val Ala Glu Val Thr
65                  70                  75                  80 gcc ttc cga ggg agc ctg cta agc tgg tac gac caa gag aaa cgg gac       288
Ala Phe Arg Gly Ser Leu Leu Ser Trp Tyr Asp Gln Glu Lys Arg Asp
                85                  90                  95 cta cca tgg aga aga cgg gca gaa gat gag atg gac ctg gac agg cgg       336
Leu Pro Trp Arg Arg Arg Ala Glu Asp Glu Met Asp Leu Asp Arg Arg
            100                 105                 110
```

```
gca tat gct gtg tgg gtc tca gag gtc atg ctg cag cag acc cag gtt    384
Ala Tyr Ala Val Trp Val Ser Glu Val Met Leu Gln Gln Thr Gln Val
        115                 120                 125 gcc act gtg atc aac tac tat acc gga tgg atg cag aag tgg cct aca    432
Ala Thr Val Ile Asn Tyr Tyr Thr Gly Trp Met Gln Lys Trp Pro Thr
130                 135                 140 ctg cag gac ctg gcc agt gct tcc ctg gag gag gtg aat caa ctc tgg    480
Leu Gln Asp Leu Ala Ser Ala Ser Leu Glu Glu Val Asn Gln Leu Trp
145                 150                 155                 160 gct ggc ctg ggc tac tat tct cgt ggc cgg cgg ctg cag gag gga gct    528
Ala Gly Leu Gly Tyr Tyr Ser Arg Gly Arg Arg Leu Gln Glu Gly Ala
                165                 170                 175 cgg aag gtg gta gag gag cta ggg ggc cac atg cca cgt aca gca gag    576
Arg Lys Val Val Glu Glu Leu Gly Gly His Met Pro Arg Thr Ala Glu
        180                 185                 190 acc ctg cag cag ctc ctg cct ggc gtg ggg cgc tac aca gct ggg gcc    624
Thr Leu Gln Gln Leu Leu Pro Gly Val Gly Arg Tyr Thr Ala Gly Ala
            195                 200                 205 att gcc tct atc gcc ttt ggc cag gca acc ggt gtg gtg gat ggc aac    672
Ile Ala Ser Ile Ala Phe Gly Gln Ala Thr Gly Val Val Asp Gly Asn
210                 215                 220 gta gca cgg gtg ctg tgc cgt gtc cga gcc att ggt gct gat ccc agc    720
Val Ala Arg Val Leu Cys Arg Val Arg Ala Ile Gly Ala Asp Pro Ser
225                 230                 235                 240 agc acc ctt gtt tcc cag cag ctc tgg ggt cta gcc cag cag ctg gtg    768
Ser Thr Leu Val Ser Gln Gln Leu Trp Gly Leu Ala Gln Gln Leu Val
                245                 250                 255 gac cca gcc cgg cca gga gat ttc aac caa gca gcc atg gag cta ggg    816
Asp Pro Ala Arg Pro Gly Asp Phe Asn Gln Ala Ala Met Glu Leu Gly
            260                 265                 270 gcc aca gtg tgt acc cca cag cgc cca ctg tgc agc cag tgc cct gtg    864
Ala Thr Val Cys Thr Pro Gln Arg Pro Leu Cys Ser Gln Cys Pro Val
        275                 280                 285 gag agc ctg tgc cgg gca cgc cag aga gtg gag cag gaa cag ctc tta    912
Glu Ser Leu Cys Arg Ala Arg Gln Arg Val Glu Gln Glu Gln Leu Leu
290                 295                 300 gcc tca ggg agc ctg tcg ggc agt cct gac gtg gag gag tgt gct ccc    960
Ala Ser Gly Ser Leu Ser Gly Ser Pro Asp Val Glu Glu Cys Ala Pro
305                 310                 315                 320 aac act gga tag tgc cac ctg tgc ctg cct ccc tcg gag ccc tgg gac   1008
Asn Thr Gly     Cys His Leu Cys Leu Pro Pro Ser Glu Pro Trp Asp
                    325                 330                 335 cag acc ctg gga gtg gtc aac ttc ccc aga aag gcc agc cgc aag ccc   1056
Gln Thr Leu Gly Val Val Asn Phe Pro Arg Lys Ala Ser Arg Lys Pro
            340                 345                 350 ccc agg gag gag agc tct gcc acc tgt gtt ctg gaa cag cct ggg gcc   1104
Pro Arg Glu Glu Ser Ser Ala Thr Cys Val Leu Glu Gln Pro Gly Ala
        355                 360                 365 ctt ggg gcc caa att ctg ctg gtg cag agg ccc aac tca ggt ctg ctg   1152
Leu Gly Ala Gln Ile Leu Leu Val Gln Arg Pro Asn Ser Gly Leu Leu
370                 375                 380 gca gga ctg tgg gag ttc ccg tcc gtg acc tgg gag ccc tca gag cag   1200
Ala Gly Leu Trp Glu Phe Pro Ser Val Thr Trp Glu Pro Ser Glu Gln
385                 390                 395 ctt cag cgc aag gcc ctg ctg cag gaa cta cag cgt tgg gct ggg ccc   1248
Leu Gln Arg Lys Ala Leu Leu Gln Glu Leu Gln Arg Trp Ala Gly Pro
400                 405                 410                 415 ctc cca gcc acg cac ctc cgg cac ctt ggg gag gtt gtc cac acc ttc   1296
Leu Pro Ala Thr His Leu Arg His Leu Gly Glu Val Val His Thr Phe
```

-continued

```
                        420                 425                 430
tct cac atc aag ctg aca tat caa gta tat ggg ctg gcc ttg gaa ggg        1344
Ser His Ile Lys Leu Thr Tyr Gln Val Tyr Gly Leu Ala Leu Glu Gly
            435                 440                 445 cag acc cca gtg acc acc gta cca cca ggt gct cgc tgg ctg acg cag        1392
Gln Thr Pro Val Thr Thr Val Pro Pro Gly Ala Arg Trp Leu Thr Gln
            450                 455                 460 gag gaa ttt cac acc gca gct gtt tcc acc gcc atg aaa aag gtt ttc        1440
Glu Glu Phe His Thr Ala Ala Val Ser Thr Ala Met Lys Lys Val Phe
465                 470                 475 cgt gtg tat cag ggc caa cag cca ggg acc tgt atg ggt tcc aaa agg        1488
Arg Val Tyr Gln Gly Gln Gln Pro Gly Thr Cys Met Gly Ser Lys Arg
480                 485                 490                 495 tcc cag gtg tcc tct ccg tgc agt cgg aaa aag ccc gcc atg ggc cag        1536
Ser Gln Val Ser Ser Pro Cys Ser Arg Lys Lys Pro Arg Met Gly Gln
                500                 505                 510 caa gtc ctg gat aat ttc ttt cgg tct cac atc tcc act gat gca cac        1584
Gln Val Leu Asp Asn Phe Phe Arg Ser His Ile Ser Thr Asp Ala His
            515                 520                 525 agc ctc aac agt gca gcc cag tga                                        1608
Ser Leu Asn Ser Ala Ala Gln
            530

<210> SEQ ID NO 4
<211> LENGTH: 1608
<212> TYPE: DNA
<213> ORGANISM: Homo sapiens
<220> FEATURE:
<221> NAME/KEY: exon
<222> LOCATION: (1)..(1608)

<400> SEQUENCE: 4 atg aca ccg ctc gtc tcc cgc ctg agt cgt ctg tgg gcc atc atg agg        48
Met Thr Pro Leu Val Ser Arg Leu Ser Arg Leu Trp Ala Ile Met Arg
1               5                   10                  15 aag cca cga gca gcc gtg gga agt ggt cac agg aag cag gca gcc agc        96
Lys Pro Arg Ala Ala Val Gly Ser Gly His Arg Lys Gln Ala Ala Ser
                20                  25                  30 cag gaa ggg agg cag aag cat gct aag aac aac agt cag gcc aag cct        144
Gln Glu Gly Arg Gln Lys His Ala Lys Asn Asn Ser Gln Ala Lys Pro
            35                  40                  45 tct gcc tgt gat ggc ctg gcc agg cag ccg gaa gag gtg gta ttg cag        192
Ser Ala Cys Asp Gly Leu Ala Arg Gln Pro Glu Glu Val Val Leu Gln
        50                  55                  60 gcc tct gtc tcc tca tac cat cta ttc aga gac gta gct gaa gtc aca        240
Ala Ser Val Ser Ser Tyr His Leu Phe Arg Asp Val Ala Glu Val Thr
65                  70                  75                  80 gcc ttc cga ggg agc ctg cta agc tgg tac gac caa gag aaa cgg gac        288
Ala Phe Arg Gly Ser Leu Leu Ser Trp Tyr Asp Gln Glu Lys Arg Asp
                85                  90                  95 cta cca tgg aga aga cgg gca gaa gat gag atg gac ctg gac agg cgg        336
Leu Pro Trp Arg Arg Arg Ala Glu Asp Glu Met Asp Leu Asp Arg Arg
            100                 105                 110 gca tat gct gtg agg gtc tca gag gtc atg ctg cag cag acc cag gtt        384
Ala Tyr Ala Val Arg Val Ser Glu Val Met Leu Gln Gln Thr Gln Val
        115                 120                 125 gcc act gtg atc aac tac tat acc gga tgg atg cag aag tgg cct aca        432
Ala Thr Val Ile Asn Tyr Tyr Thr Gly Trp Met Gln Lys Trp Pro Thr
    130                 135                 140 ctg cag gac ctg gcc agt gct tcc ctg gag gag gtg aat caa ctc tgg        480
Leu Gln Asp Leu Ala Ser Ala Ser Leu Glu Glu Val Asn Gln Leu Trp
```

```
                145                 150                 155                 160
gct ggc ctg ggc tac tat tct cgt ggc cgg cgg ctg cag gag gga gct    528
Ala Gly Leu Gly Tyr Tyr Ser Arg Gly Arg Arg Leu Gln Glu Gly Ala
                165                 170                 175 cgg aag gtg gta gag gag cta ggg ggc cac atg cca cgt aca gca gag    576
Arg Lys Val Val Glu Glu Leu Gly Gly His Met Pro Arg Thr Ala Glu
            180                 185                 190 acc ctg cag cag ctc ctg cct ggc gtg ggg cgc tac aca gct ggg gcc    624
Thr Leu Gln Gln Leu Leu Pro Gly Val Gly Arg Tyr Thr Ala Gly Ala
            195                 200                 205 att gcc tct atc gcc ttt ggc cag gca acc ggt gtg gtg gat ggc aac    672
Ile Ala Ser Ile Ala Phe Gly Gln Ala Thr Gly Val Val Asp Gly Asn
            210                 215                 220 gta gca cgg gtg ctg tgc cgt gtc cga gcc att ggt gct gat ccc agc    720
Val Ala Arg Val Leu Cys Arg Val Arg Ala Ile Gly Ala Asp Pro Ser
225                 230                 235                 240 agc acc ctt gtt tcc cag cag ctc tgg ggt cta gcc cag cag ctg gtg    768
Ser Thr Leu Val Ser Gln Gln Leu Trp Gly Leu Ala Gln Gln Leu Val
                245                 250                 255 gac cca gcc cgg cca gga gat ttc aac caa gca gcc atg gag cta ggg    816
Asp Pro Ala Arg Pro Gly Asp Phe Asn Gln Ala Ala Met Glu Leu Gly
            260                 265                 270 gcc aca gtg tgt acc cca cag cgc cca ctg tgc agc cag tgc cct gtg    864
Ala Thr Val Cys Thr Pro Gln Arg Pro Leu Cys Ser Gln Cys Pro Val
            275                 280                 285 gag agc ctg tgc cgg gca cgc cag aga gtg gag cag gaa cag ctc tta    912
Glu Ser Leu Cys Arg Ala Arg Gln Arg Val Glu Gln Glu Gln Leu Leu
            290                 295                 300 gcc tca ggg agc ctg tcg ggc agt cct gac gtg gag gag tgt gct ccc    960
Ala Ser Gly Ser Leu Ser Gly Ser Pro Asp Val Glu Glu Cys Ala Pro
305                 310                 315                 320 aac act gga cag tgc cac ctg tgc ctg cct ccc tcg gag ccc tgg gac    1008
Asn Thr Gly Gln Cys His Leu Cys Leu Pro Pro Ser Glu Pro Trp Asp
                325                 330                 335 cag acc ctg gga gtg gtc aac ttc ccc aga aag gcc agc cgc aag ccc    1056
Gln Thr Leu Gly Val Val Asn Phe Pro Arg Lys Ala Ser Arg Lys Pro
            340                 345                 350 ccc agg gag gag agc tct gcc acc tgt gtt ctg gaa cag cct ggg gcc    1104
Pro Arg Glu Glu Ser Ser Ala Thr Cys Val Leu Glu Gln Pro Gly Ala
            355                 360                 365 ctt ggg gcc caa att ctg ctg gtg cag agg ccc aac tca ggt ctg ctg    1152
Leu Gly Ala Gln Ile Leu Leu Val Gln Arg Pro Asn Ser Gly Leu Leu
370                 375                 380 gca gga ctg tgg gag ttc ccg tcc gtg acc tgg gag ccc tca gag cag    1200
Ala Gly Leu Trp Glu Phe Pro Ser Val Thr Trp Glu Pro Ser Glu Gln
385                 390                 395                 400 ctt cag cgc aag gcc ctg ctg cag gaa cta cag cgt tgg gct ggg ccc    1248
Leu Gln Arg Lys Ala Leu Leu Gln Glu Leu Gln Arg Trp Ala Gly Pro
                405                 410                 415 ctc cca gcc acg cac ctc cgg cac ctt ggg gag gtt gtc cac acc ttc    1296
Leu Pro Ala Thr His Leu Arg His Leu Gly Glu Val Val His Thr Phe
            420                 425                 430 tct cac atc aag ctg aca tat caa gta tat ggg ctg gcc ttg gaa ggg    1344
Ser His Ile Lys Leu Thr Tyr Gln Val Tyr Gly Leu Ala Leu Glu Gly
            435                 440                 445 cag acc cca gtg acc acc gta cca cca ggt gct cgc tgg ctg acg cag    1392
Gln Thr Pro Val Thr Thr Val Pro Pro Gly Ala Arg Trp Leu Thr Gln
450                 455                 460 gag gaa ttt cac acc gca gct gtt tcc acc gcc atg aaa aag gtt ttc    1440
Glu Glu Phe His Thr Ala Ala Val Ser Thr Ala Met Lys Lys Val Phe
```

```
Glu Glu Phe His Thr Ala Ala Val Ser Thr Ala Met Lys Lys Val Phe
465                 470                 475                 480 cgt gtg tat cag ggc caa cag cca ggg acc tgt atg ggt tcc aaa agg    1488
Arg Val Tyr Gln Gly Gln Gln Pro Gly Thr Cys Met Gly Ser Lys Arg
                    485                 490                 495 tcc cag gtg tcc tct ccg tgc agt cgg aaa aag ccc cgc atg ggc cag    1536
Ser Gln Val Ser Ser Pro Cys Ser Arg Lys Lys Pro Arg Met Gly Gln
                500                 505                 510 caa gtc ctg gat aat ttc ttt cgg tct cac atc tcc act gat gca cac    1584
Gln Val Leu Asp Asn Phe Phe Arg Ser His Ile Ser Thr Asp Ala His
        515                 520                 525 agc ctc aac agt gca gcc cag tga                                    1608
Ser Leu Asn Ser Ala Ala Gln
        530                 535

<210> SEQ ID NO 5
<211> LENGTH: 19
<212> TYPE: DNA
<213> ORGANISM: Homo sapiens

<400> SEQUENCE: 5
gaagctgcgg gagctgaaa                                                 19

<210> SEQ ID NO 6
<211> LENGTH: 19
<212> TYPE: DNA
<213> ORGANISM: Homo sapiens

<400> SEQUENCE: 6
atccccgact gcctgaacc                                                 19

<210> SEQ ID NO 7
<211> LENGTH: 20
<212> TYPE: DNA
<213> ORGANISM: Homo sapiens

<400> SEQUENCE: 7
ctgcatttgg ctgggtcttt                                                20

<210> SEQ ID NO 8
<211> LENGTH: 20
<212> TYPE: DNA
<213> ORGANISM: Homo sapiens

<400> SEQUENCE: 8
cgcacctggc ccttagtaag                                                20

<210> SEQ ID NO 9
<211> LENGTH: 20
<212> TYPE: DNA
<213> ORGANISM: Homo sapiens

<400> SEQUENCE: 9
agcctgtgca gggatgattg                                                20

<210> SEQ ID NO 10
<211> LENGTH: 22
<212> TYPE: DNA
<213> ORGANISM: Homo sapiens

<400> SEQUENCE: 10
caaccccaga tgaggagtta gg                                             22
```

```
<210> SEQ ID NO 11
<211> LENGTH: 20
<212> TYPE: DNA
<213> ORGANISM: Homo sapiens

<400> SEQUENCE: 11
ctcatctggg gttgcattga                                               20

<210> SEQ ID NO 12
<211> LENGTH: 20
<212> TYPE: DNA
<213> ORGANISM: Homo sapiens

<400> SEQUENCE: 12
gggttggcat gaggacactg                                               20

<210> SEQ ID NO 13
<211> LENGTH: 18
<212> TYPE: DNA
<213> ORGANISM: Homo sapiens

<400> SEQUENCE: 13
gggcaggtca gcagtgtc                                                 18

<210> SEQ ID NO 14
<211> LENGTH: 20
<212> TYPE: DNA
<213> ORGANISM: Homo sapiens

<400> SEQUENCE: 14
tacacccacc ccaaagtaga                                               20

<210> SEQ ID NO 15
<211> LENGTH: 20
<212> TYPE: DNA
<213> ORGANISM: Homo sapiens

<400> SEQUENCE: 15
tactttgggg tgggtgtaga                                               20

<210> SEQ ID NO 16
<211> LENGTH: 20
<212> TYPE: DNA
<213> ORGANISM: Homo sapiens

<400> SEQUENCE: 16
aagagatcac ccgtcagtcc                                               20

<210> SEQ ID NO 17
<211> LENGTH: 20
<212> TYPE: DNA
<213> ORGANISM: Homo sapiens

<400> SEQUENCE: 17
gggactgacg ggtgatctct                                               20

<210> SEQ ID NO 18
<211> LENGTH: 22
<212> TYPE: DNA
<213> ORGANISM: Homo sapiens

<400> SEQUENCE: 18
ttggagtgca agactcaaga tt                                            22
```

<210> SEQ ID NO 19
<211> LENGTH: 20
<212> TYPE: DNA
<213> ORGANISM: Homo sapiens

<400> SEQUENCE: 19
ccaggagtct tgggtgtctt                                               20

<210> SEQ ID NO 20
<211> LENGTH: 20
<212> TYPE: DNA
<213> ORGANISM: Homo sapiens

<400> SEQUENCE: 20
agaggggcca aagagttagc                                               20

<210> SEQ ID NO 21
<211> LENGTH: 20
<212> TYPE: DNA
<213> ORGANISM: Homo sapiens

<400> SEQUENCE: 21
aactctttgg cccctctgtg                                               20

<210> SEQ ID NO 22
<211> LENGTH: 21
<212> TYPE: DNA
<213> ORGANISM: Homo sapiens

<400> SEQUENCE: 22
gaagggaaca ctgctgtgaa g                                             21

<210> SEQ ID NO 23
<211> LENGTH: 19
<212> TYPE: DNA
<213> ORGANISM: Homo sapiens

<400> SEQUENCE: 23
gtgcttcagg ggtgtctgc                                                19

<210> SEQ ID NO 24
<211> LENGTH: 22
<212> TYPE: DNA
<213> ORGANISM: Homo sapiens

<400> SEQUENCE: 24
tgtcataggg cagagtcact cc                                            22

<210> SEQ ID NO 25
<211> LENGTH: 22
<212> TYPE: DNA
<213> ORGANISM: Homo sapiens

<400> SEQUENCE: 25
taaggagtga ctctgcccta tg                                            22

<210> SEQ ID NO 26
<211> LENGTH: 18
<212> TYPE: DNA
<213> ORGANISM: Homo sapiens

<400> SEQUENCE: 26

-continued

```
gccaagaggg gctttagg                                           18

<210> SEQ ID NO 27
<211> LENGTH: 20
<212> TYPE: DNA
<213> ORGANISM: Homo sapiens

<400> SEQUENCE: 27
agcccctctt ggcttgagta                                         20

<210> SEQ ID NO 28
<211> LENGTH: 19
<212> TYPE: DNA
<213> ORGANISM: Homo sapiens

<400> SEQUENCE: 28
tgccgattcc ctccattct                                          19

<210> SEQ ID NO 29
<211> LENGTH: 20
<212> TYPE: DNA
<213> ORGANISM: Homo sapiens

<400> SEQUENCE: 29
agggcagtgg catgagtaac                                         20

<210> SEQ ID NO 30
<211> LENGTH: 20
<212> TYPE: DNA
<213> ORGANISM: Homo sapiens

<400> SEQUENCE: 30
ggctattccg ctgctcactt                                         20

<210> SEQ ID NO 31
<211> LENGTH: 21
<212> TYPE: DNA
<213> ORGANISM: Homo sapiens

<400> SEQUENCE: 31
ttggcttttg aggctatatc c                                       21

<210> SEQ ID NO 32
<211> LENGTH: 23
<212> TYPE: DNA
<213> ORGANISM: Homo sapiens

<400> SEQUENCE: 32
catgtaggaa acacaaggaa gta                                     23

<210> SEQ ID NO 33
<211> LENGTH: 21
<212> TYPE: DNA
<213> ORGANISM: Homo sapiens

<400> SEQUENCE: 33
tgaagttaag ggcagaacac c                                       21

<210> SEQ ID NO 34
<211> LENGTH: 22
<212> TYPE: DNA
<213> ORGANISM: Homo sapiens

<400> SEQUENCE: 34
```

```
gttcacccag acattcgtta gt                                              22

<210> SEQ ID NO 35
<211> LENGTH: 22
<212> TYPE: DNA
<213> ORGANISM: Homo sapiens

<400> SEQUENCE: 35
aggacaagga gaggattctc tg                                              22

<210> SEQ ID NO 36
<211> LENGTH: 18
<212> TYPE: DNA
<213> ORGANISM: Homo sapiens

<400> SEQUENCE: 36
ggaatggggg ctttcaga                                                   18
```

US 7,393,940 B2

SCREENING METHODS AND SEQUENCES RELATING THERETO

CROSS-REFERENCE TO RELATED APPLICATIONS

This application is a continuation-in-part of PCT application No. PCT/GB2003/001656, filed Apr. 16, 2003, which claims priority to GB 0308241.9 filed Apr. 10, 2003, both of which are hereby incorporated by reference in their entireties.

FIELD OF THE INVENTION

The present invention relates to inherited variations in genes believed to be involved in base excision repair (BER) pathways of humans; to the use of these variants in screening patients for defects in BER and thereby for cancers or predisposition to cancers. The invention further relates to screening methods using the variants, and to a diagnostic kit, and parts thereof, for use in the screening methods.

BACKGROUND OF THE INVENTION

BER pathways play a major role in the repair of mutations caused by reactive oxygen species that are generated during aerobic metabolism, as described in Nature 362, 709-715 (1993). Oxidative DNA damage has been implicated in the aetiology of degenerative diseases, ageing and cancer (Mutat. Res. 250, 3116 (1991), but evidence linking inherited deficiencies of BER to these diseases has, until recently, been lacking.

8-Oxo-7,8-dihydrodeoxyguanine (8-oxoG), the most stable product of oxidative DNA damage, is highly mutagenic, since it readily mispairs with A residues (Nature 349, 431-434 (1991)), leading to an increased frequency of spontaneous G:C→T:A transversion mutations in repair-deficient bacteria and yeast cells. In *E. coli*, three enzymes, mutM, mutY and mutT, function synergistically to protect cells from the deleterious effects of guanine oxidation (J Bacteriol. 174, 6321-6325(1992)). The mutM DNA glycosylase removes the oxidised base from 8-oxoG:C base pairs in duplex DNA; the mutY DNA glycosylase excises A residues misincorporated opposite unrepaired 8-oxoG during replication; and mutT is an 8-oxo-dGTPase preventing incorporation of 8-oxo-dGMP into nascent DNA. Human mutM, mutY and mutT homologues have been identified and termed hOGG1 (Proc. Natl. Acad. Sci.(USA) 94,8016-8020 (1997)), hMYH (or MYH) (J. Bactiol. 178, 3885-3892(1996)) and hMTH (J. Biol. Chem. 268,23524-23530 (1993)), respectively. Patent specification No. WO 97/33903 also discloses a human MutY polypeptide and DNA encoding it, together with its potential use in diagnosing a cancer or a susceptibility to a cancer.

Very recently in our International Patent Application WO (PCT/GB2002/003591) we have shown that mutations in the human base excision repair gene MYH (Accession No. NM_012222) cause an autosomal recessive trait characterised by multiple colorectal adenomas and high colorectal cancer risk.

Registers for patients and families with colorectal polyposis are widely established at regional or national level in many countries. They serve to co-ordinate proactive genetic testing, colonoscopic surveillance and surgical management across extended families. In the United Kingdom most polyposis registers are managed by regional clinical genetics services covering geographically defined populations of one to five million. The most important form of colorectal polyposis is familial adenomatous polyposis (FAP), an autosomal dominant disorder caused by mutations of the *adenomatous polyposis coli* (APC) gene. FAP is associated with hundreds or thousands of adenomatous polyps and leads to colorectal cancer in virtually all cases unless treated by prophylactic colectomy. Traditionally, all patients with >100 macroscopic colorectal adenomas are diagnosed as FAP. Classification of cases with less than 100 adenomas has been problematic. Some are associated with inherited mutations at specific locations within the APC gene and are classified as attenuated FAP (AFAP). The possible importance of other loci has been unclear.

The prevalence of MYH polyposis is unknown but it is unlikely to be confused with FAP or AFAP in families showing vertical transmission of polyposis. However, many patients with FAP/AFAP or with multiple colorectal adenomas (with or without colorectal cancer) occur as sporadic cases and others may have affected siblings with unaffected parents. Such cases may result from de novo APC gene mutations or gonadal mosaicism in a clinically unaffected parent. However, we hypothesised that some cases might be attributable to undiagnosed recessively transmitted MYH polyposis. If correct this would have important implications for family management. If an APC gene mutation is assumed, management for relatives of sporadic cases is based on a 1-in-2 risk to their offspring but a very low risk to their siblings. By contrast, the risks associated with MYH polyposis are 1-in-4 for the siblings of apparently sporadic cases, but extremely low for their offspring. Hence detection of MYH polyposis is important for accurate genetic counselling, genetic testing and effective planning of surveillance colonoscopy for extended families.

To identify families in which mutations of MYH rather than the APC gene might be causative, we applied the following selection criteria in six well established regional polyposis registers in the United Kingdom: 1) a family history showing no vertical transmission of polyposis 2) at least 10 colorectal adenomas with or without colorectal cancer in the index case 3) no clearly pathogenic mutation in the APC gene identified during genetic testing. We then sought MYH mutations in blood DNA samples from affected index cases. In previous reports (Al-Tassan et al. Nature Genet 2002, 30:227-232; Jones et al. Hum Mol Genet 2002, 11: 2961-7; Sieber et al. New Engl. J. Med. 2003, 348: 791-799), 31 out of 36 mutant alleles characterised in Caucasian patients with biallelic MYH mutations and colorectal polyposis were either Y165C (18 alleles) or G382D (13 alleles). Therefore, in Caucasian index cases we first assayed for these mutations by sequencing of exon 7 (for Y165C) and by BglII restriction enzyme digestion (for G382D). In cases heterozygous for either Y165C or G382D we screened for mutations affecting the second MYH allele by sequencing its 16 coding exons. Since different MYH mutations appear to be important in non-Caucasians (Jones et al. Hum Mol Genet 2002, 11: 2961-7) we sequenced all exons of MYH in all non-Caucasian index cases.

In addition to the mutations that we have previously identified in MYH (International Patent Application WO PCT/GB2002/003591), we identified four novel mutations: Q324X (C to T at nucleotide 970), W117R (T to A at nucleotide 349), 347−1 G to A and 891+3 A to C.

DETAILED DESCRIPTION OF INVENTION

Definitions

The terms "genetic variant" and "nucleotide variant" are used herein interchangeably to refer to changes or alterations to the reference human MYH gene or cDNA sequence at a particular locus, including, but not limited to, nucleotide base deletions, insertions, inversions, and substitutions in the coding and noncoding regions. Deletions may be of a single nucleotide base, a portion or a region of the nucleotide sequence of the gene, or of the entire gene sequence. Insertions may be of one or more nucleotide bases. The "genetic variant" or "nucleotide variants" may occur in transcriptional regulatory regions, untranslated regions of mRNA, exons, introns, or exon/intron junctions. The "genetic variant" or "nucleotide variants" may or may not result in stop codons, frame shifts, deletions of amino acids, altered gene transcript splice forms or altered amino acid sequence.

The term "allele" or "gene allele" is used herein to refer generally to a naturally occurring gene having a reference sequence or a gene containing a specific nucleotide variant.

As used herein, "haplotype" is a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human MYH protein sequence resulting from "genetic variants" or "nucleotide variants" to the reference human gene encoding the reference MYH protein. The term "amino acid variant" is intended to encompass not only single amino acid substitutions, but also amino acid deletions, insertions, and other significant changes of amino acid sequence in the reference MYH protein.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

As used herein, the term "MYH nucleic acid" means a nucleic acid molecule the nucleotide sequence of which is uniquely found in an MYH gene. That is, a "MYH nucleic acid" is either an MYH genomic DNA or mRNA/cDNA, having a naturally existing nucleotide sequence encoding a naturally existing MYH protein (wild-type or mutant form). The sequence of an example of a naturally existing MYH nucleic acid is found in GenBank Accession No. U63329 (PRI 28-JUL-1996).

As used herein, the term "MYH protein" means a polypeptide molecule the amino acid sequence of which is found uniquely in an MYH protein. That is, "MYH protein" is a naturally existing MYH protein (wild-type or mutant form). The sequence of a wild-type form of a MYH protein is found in GenBank Accession No. U63329 (PRI 28-JUL-1996).

The term "locus" refers to a specific position or site in a gene sequence or protein. Thus, there may be one or more contiguous nucleotides in a particular gene locus, or one or more amino acids at a particular locus in a polypeptide. Moreover, "locus" may also be used to refer to a particular position in a gene where one or more nucleotides have been deleted, inserted, or inverted.

As used herein, the terms "polypeptide," "protein," and "peptide" are used interchangeably to refer to an amino acid chain in which the amino acid residues are linked by covalent peptide bonds. The amino acid chain can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The terms "primer", "probe," and "oligonucleotide" are used herein interchangeably to refer to a relatively short nucleic acid fragment or sequence. They can be DNA, RNA, or a hybrid thereof, or chemically modified analog or derivatives thereof. Typically, they are single-stranded. However, they can also be double-stranded having two complementing strands which can be separated apart by denaturation. Normally, they have a length of from about 8 nucleotides to about 200 nucleotides, preferably from about 12 nucleotides to about 100 nucleotides, and more preferably about 18 to about 50 nucleotides. They can be labeled with detectable markers or modified in any conventional manners for various molecular biological applications.

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Specifically, since a naturally existing chromosome (or a viral equivalent thereof) includes a long nucleic acid sequence, an "isolated nucleic acid" as used herein means a nucleic acid molecule having only a portion of the nucleic acid sequence in the chromosome but not one or more other portions present on the same chromosome. More specifically, an "isolated nucleic acid" typically includes no more than 25 kb naturally occurring nucleic acid sequences which immediately flank the nucleic acid in the naturally existing chromosome (or a viral equivalent thereof). However, it is noted that an "isolated nucleic acid" as used herein is distinct from a clone in a conventional library such as genomic DNA library and cDNA library in that the clone in a library is still in admixture with almost all the other nucleic acids of a chromosome or cell. Thus, an "isolated nucleic acid" as used herein also should be substantially separated from other naturally occurring nucleic acids that are on a different chromosome of the same organism. Specifically, an "isolated nucleic acid" means a composition in which the specified nucleic acid molecule is significantly enriched so as to constitute at least 10% of the total nucleic acids in the composition.

An "isolated nucleic acid" can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed), or can be a chemically synthesized nucleic acid having a naturally occurring nucleotide sequence or an artificially modified form thereof.

The term "isolated polypeptide" as used herein is defined as a polypeptide molecule that is present in a form other than that found in nature. Thus, an isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a composition or preparation in which the specified polypeptide molecule is significantly enriched so as to constitute at least 10% of the total protein content in the composition. A "purified polypeptide" can be obtained from natural or recombinant host cells by standard purification techniques, or by chemically synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally occurring polypeptide or isolated polypeptide having a specified polypeptide molecule covalently linked to one or more other polypeptide molecules that do not link to the specified polypeptide in nature. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

The term "high stringency hybridization conditions," when used in connection with nucleic acid hybridization, means hybridization conducted overnight at 42° C. in a solution containing 50% formamide, 5×SSC (750 mM NaCl, 75 mM sodium citrate), 50 mM sodium phosphate, pH 7.6, 5× Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, means hybridization conducted overnight at 37° C. in a solution containing 50% formamide, 5×SSC (750 mM NaCl, 75 mM sodium citrate), 50 mM sodium phosphate, pH 7.6, 5× Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific "percentage identical to" another sequence (comparison sequence) in the present disclosure. In this respect, the percentage identity is determined by the algorithm of Karlin and Altschul, Proc. Natl. Acad. Sci. USA, 90:5873-5877 (1993), which is incorporated into various BLAST programs. Specifically, the percentage identity is determined by the "BLAST 2 Sequences" tool, which is available at NCBI's website. See Tatusova and Madden, FEMS Microbiol. Lett., 174(2):247-250 (1999). For pairwise DNA-DNA comparison, the BLAST 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter). Percent identity of two sequences is calculated by aligning a test sequence with a comparison sequence using BLAST 2.1.2., determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST 2.1.2 is used to compare two sequences, it aligns the sequences and yields the percent identity over defined, aligned regions. If the two sequences are aligned across their entire length, the percent identity yielded by the BLAST 2.1.1 is the percent identity of the two sequences. If BLAST 2.1.2 does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence.

The term "reference sequence" refers to a polynucleotide or polypeptide sequence known in the art, including those disclosed in publicly accessible databases, e.g., GenBank, or a newly identified gene sequence, used simply as a reference with respect to the nucleotide variants provided in the present invention. The nucleotide or amino acid sequence in a reference sequence is contrasted to the alleles disclosed in the present invention having newly discovered nucleotide or amino acid variants. For genomic DNA, the sequence in GenBank Accession No. NT_032977 (PRI 19-AUG-2004) can be used as a reference sequence (or as otherwise specified), while the nucleotide and amino acid sequences in GenBank Accession No. U63329 (PRI 28-JUL-1996) can be used as the reference sequences (or as otherwise specified) for MYH cDNA and proteins, respectively.

General Screening Methods

The present invention provides a variant of MYH, suitable for use in a screening method of the invention, comprising a nucleic acid variant selected from:
1. 347−1 G to A, as defined herein [SEQ ID No: 1];
2. 891+3 A to C, as defined herein [SEQ ID No: 2];

or a nucleic acid or polypeptide variant selected from:
3. Q324X (C to T at nucleotide 970), as defined herein [SEQ ID No: 3]; and
4. W117R (T to A at nucleotide 349), as defined herein [SEQ ID No: 4].

The present invention also provides nucleic acid molecules and corresponding polypeptides molecules, and vice versa that are variants of the human MYH gene (historically designated hMYH and more recently designated just MYH).

Accordingly the present invention further provides:
(a) a nucleic acid molecule encoding one or more of the human MYH variants herein described with reference to SEQ ID No: 1, 2, 3 or 4; or
(b) a nucleic acid molecule substantially homologous to that identified in (a) above; or
(c) a nucleic acid molecule that hybridises to, at least, the region of said nucleic acid molecule in (a) or (b) above that contains said variant; or
(d) an oligonucleotide specific for any of the aforementioned molecules.

Reference herein to said homologous nucleic acid molecule in (b) above comprises reference to a molecule that displays the same function and biological activity as the nucleic acid molecule described in (a) above. More preferably still, said homologues are at least 90% identical to the nucleic acid molecule described in (a) above.

In a preferred embodiment of the invention said oligonucleotide specific for any of the aforementioned molecules includes any one or more of the oligonucleotides listed in Table 1 herein.

According to a further aspect of the invention there is provided the polypeptides encoded by the nucleic acid molecule variants of the invention.

According to a yet further aspect of the invention there is provided:

(a) a polypeptide comprising one or more of the human MYH variants herein described with reference to SEQ ID No: 1, 2, 3 or 4; or
(b) a polypeptide substantially homologous to that identified in (a) above; or
(c) a polypeptide fragment containing the variant region of the polypeptide mentioned in (a) or (b) above.

More preferably, the polypeptide molecules of the invention are characterised by giving rise to the protein variants of the human MYH gene described herein. Particular polypeptides of the invention are Q324X and W117R as herein defined.

According to a further aspect of the invention there is provided a method for diagnosing susceptibility to cancer comprising determining, from a sample derived from a patient, a mutation comprising a variant according to this invention. In particular, there is provided a screening method for identifying an individual having a predisposition towards having a cancer.

According to a further aspect of the invention there is therefore provided a screening method for determining whether an individual has a susceptibility to, or predisposition towards, cancer comprising:

(a) obtaining a test sample from an individual to be tested comprising a nucleic acid molecule encoding the human MYH gene; and
(b) comparing the nucleic acid sequence of said nucleic acid molecule from said test sample with the wild-type nucleic acid sequence of the corresponding wild-type human MYH gene; and where there is a difference between the sequence of the test sample and the wild-type sequence concluding that the individual is predisposed towards having a cancer.

In a preferred screening method of the invention said comparison above involves looking for a variant of a nucleic acid molecule as herein described with reference to SEQ ID No: 1, 2, 3 or 4. For example, the comparison involves looking for a C to T at nucleotide 970, or T to A at nucleotide 349, or G to A at 347−1 or A to C at 891+3. In each of the aforementioned instances the initial reference number (970, 349, 347 and 891) refers to the position of the base pair within the coding region where the first base in the coding region is designated 1. The number after a + or − symbol represents the number of bases into the non-coding (intronic) sequence either upstream (+) or downstream (−) of the nearest base pair in the coding (exonic) region. The nucleotide variant 347−1 A to C is present at base pair position 7084 of SEQ ID NO:1. Similarly, the 839+3 A to C is present at base pair position 8092 of SEQ ID NO:2.

In a preferred embodiment of the screening method of the invention said comparing step under (b) above involves PCR amplification of said nucleic acid molecules using any one or more of the primers illustrated in Table 1 herein.

The above screening method of the invention may be performed using a test sample containing a hMYH polypeptide and so comparing the test hMYH polypeptide with that of the wild-type to identify said variant.

Accordingly, the screening method of the invention comprises:

(a) obtaining a test sample of an individual to be tested comprising a polypeptide molecule encoding the human MYH protein; and
(b) comparing the amino acid sequence of said test protein with that of wild-type protein, and where there is a difference between the test sample and the wild-type protein, concluding that the individual is predisposed to having a cancer.

In a preferred screening method of the invention said comparison involves looking to see if amino acid Q (Glutamine) has been substituted for X [a stop codon] at position 324 or amino acid W (Tryptophan) has been substituted for amino acid R (Arginine) at position 117, where the reference numbers refer to the sequence of amino acids defining the protein.

Alternatively the screening method of the invention may be performed using an immunoassay where an antibody specific for the variant of the invention is used to determine whether an individual expresses wild-type protein or a variant as herein described. Ideally, the antibody is a monoclonal and, more ideally still, said assay is an ELISA.

It will be clear from the above that the nucleic acid molecules and polypeptide molecules described herein, and termed variants of the invention, have diagnostic purpose and accordingly their corresponding sequences can be used in diagnostic assays in order to determine whether an individual has a significant variant in his/her MYH gene which in turn encodes a significant MYH protein variant. Accordingly, the sequences described herein are of diagnostic use and may be provided in the diagnostic kit for determining the susceptibility or predisposition to cancer.

In the above described methods the diagnostic techniques may be undertaken to identify any cancer but particularly bowel cancer (i.e. large intestine).

According to a yet further aspect of the invention there is provided the use of:

(a) a variant human MYH gene or protein as herein described; or
(b) a gene or protein homologous thereto; or
(c) a nucleic acid molecule, or a polypeptide, that hybridises to, or contains, respectively, the region of said variant gene or protein as herein described;

in a therapeutic, diagnostic or detection method.

According to a yet further aspect of the invention there is provided a kit suitable for use in carrying out the screening method of the invention which kit comprises one or more of:

(a) a nucleic acid molecule containing a variant of the human MYH gene as herein defined;
(b) a polypeptide containing a variant of the human MYH gene as herein defined;
(c) a nucleic acid molecule encoding the wild-type of the human MYH protein;
(d) a wild-type human MYH protein; or
(e) one or more reagents suitable for carrying out PCR for amplifying desired regions of a patient's DNA or protein.

In accordance with yet another aspect of the present invention, a method is provided for genotyping the MYH gene of an individual by determining whether the individual has a genetic variant or an amino acid variant provided in accordance with the present invention. In addition, the present invention also provides a method for predicting in an individual a predisposition to cancer (e.g., colorectal cancer). The method comprises the step of detecting in the individual the presence or absence of a genetic variant or amino acid variant provided according to the present invention.

In a preferred kit of the invention said reagents include, for example, PCR primers corresponding to regions of the human MYH gene containing the variants of the invention. Preferably, these primers are oligonucleotides comprising 5 to 30 bases and are selected so as to be specific for the variant of interest.

Nucleic Acids

The present invention also encompasses an isolated nucleic acid comprising the nucleotide sequence of a region of a MYH genomic DNA or cDNA or mRNA, wherein the region contains one or more nucleotide variants of the invention as described above, or one or more nucleotide variants that will give rise to one or more amino acid variants as described above, or the complement thereof. Such regions can be isolated and analyzed to efficiently detect the nucleotide variants of the present invention. Also, such regions can also be isolated and used as probes or primers in detection of the nucleotide variants of the present invention and other uses as will be clear from the descriptions below.

Accordingly, the present invention provides an isolated MYH nucleic acid containing at least one of the newly discovered nucleotide variants as described above, or one or more nucleotide variants that will result in the amino acid variants of the invention. The term "MYH nucleic acid" is as defined above and means a naturally existing nucleic acid coding for a wild-type or variant or mutant MYH. The term "MYH nucleic acid" is inclusive and may be in the form of either double-stranded or single-stranded nucleic acids, and a single strand can be either of the two complementing strands. The isolated MYH nucleic acid can be naturally existing genomic DNA, mRNA or cDNA.

In another embodiment, the isolated MYH nucleic acid has a nucleotide sequence that is at least 95%, preferably at least 97% and more preferably at least 99% identical to one or more of SEQ ID NO:1-SEQ ID NO:4 that contains one or more exonic nucleotide variants of invention.

In yet another embodiment, the isolated MYH nucleic acid has a nucleotide sequence encoding MYH protein having an amino acid sequence that contains one or more amino acid variants of the invention. Isolated MYH nucleic acids having a nucleotide sequence that is the complement of the sequence are also encompassed by the present invention.

In yet another embodiment, the isolated MYH nucleic acid has a nucleotide sequence encoding a MYH protein having an amino acid sequence that is at least 95%, preferably at least 97% and more preferably at least 99% identical to one or more of SEQ ID NO:1-SEQ ID NO:4 that contains one or more amino acid variants of the invention, or the complement thereof.

The present invention also provides an isolated nucleic acid, naturally occurring or artificial, having a nucleotide sequence that is at least 95%, preferably at least 97% and more preferably at least 99% identical to one or more of SEQ ID NO:1-SEQ ID NO:4 that contains one or more of the nucleotide variants of the invention, or the complement thereof.

In another embodiment, the present invention provides an isolated nucleic acid, naturally occurring or artificial, having a nucleotide sequence encoding a MYH protein having an amino acid sequence according to one or more of SEQ ID NO:1-SEQ ID NO:4 that contains one or more amino acid variants of the invention. Isolated nucleic acids having a nucleotide sequence that is the complement of the sequence are also encompassed by the present invention.

In addition, isolated nucleic acids are also provided which have a nucleotide sequence encoding a protein having an amino acid sequence that is at least 95%, preferably at least 97% and more preferably at least 99% identical to one or more of the amino acid sequences in SEQ ID NO:1-SEQ ID NO:4 that contains one or more amino acid variants of the invention, or the complement thereof.

The present invention also encompasses an isolated nucleic acid comprising the nucleotide sequence of a region of a MYH genomic DNA or cDNA or mRNA, wherein the region contains one or more nucleotide variants as provided by the, or one or more nucleotide variants that will give rise to one or more amino acid variants of the invention, or the complement thereof. Such regions can be isolated and analyzed to efficiently detect the nucleotide variants of the present invention. Also, such regions can also be isolated and used as probes or primers in detection of the nucleotide variants of the present invention and other uses as will be clear from the descriptions below.

Thus, in one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of a MYH nucleic acid, the contiguous span containing one or more nucleotide variants of the invention, or the complement thereof. In specific embodiments, the isolated nucleic acid are oligonucleotides having a contiguous span of from about 17, 18, 19, 20, 21, 22, 23 or 25 to about 30, 40 or 50, preferably from about 21 to about 30 nucleotide residues, of any MYH nucleic acid, said contiguous span containing one or more nucleotide variants of the invention.

In one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of one or more nucleotide variants of the invention, or the complement thereof. In specific embodiments, the isolated nucleic acid comprises a nucleotide sequence according to SEQ ID NO:1. In specific embodiments, the isolated nucleic acid comprises a nucleotide sequence according to SEQ ID NO:2. In specific embodiments, the isolated nucleic acid comprises a nucleotide sequence according to SEQ ID NO:3. In specific embodiments, the isolated nucleic acid comprises a nucleotide sequence according to SEQ ID NO:4. In preferred embodiments, the isolated nucleic acid are oligonucleotides having a contiguous span of from about 17, 18, 19, 20, 21, 22, 23 or 25 to about 30, 40 or 50, preferably from about 21 to about 30 nucleotide residues, of any one of SEQ ID NO:1 through SEQ ID NO:4 containing one or more nucleotide variants of the invention. The complements of the isolated nucleic acids are also encompassed by the present invention.

In preferred embodiments, an isolated oligonucleotide of the present invention is specific to a MYH allele ("allele-specific") containing one or more nucleotide variants as disclosed in the present invention. That is, the isolated oligonucleotide is capable of selectively hybridizing, under high stringency conditions generally recognized in the art, to a MYH genomic or cDNA or mRNA containing one or more nucleotide variants as disclosed in the present invention, but not to a MYH gene having a reference sequence (e.g., wild-type). Such oligonucleotides will be useful in a hybridization-based method for detecting the nucleotide variants of the present invention as described in details below. An ordinarily skilled artisan would recognize various stringent conditions which enable the oligonucleotides of the present invention to differentiate between a MYH gene having a reference sequence and a variant MYH gene of the present invention. For example, the hybridization can be conducted overnight in a solution containing 50% formamide, 5×SSC, pH7.6, 5× Denhardt's solution, 10% dextran sulfate, and 20 microgram/ml denatured, sheared salmon sperm DNA. The hybridization filters can be washed in 0.1×SSC at about 65° C. Alternatively, typical PCR conditions employed in the art with an annealing temperature of about 55° C. can also be used.

In some embodiments of the present invention, isolated nucleic acids are provided which encode a contiguous span of at least 6, 7, 8, 9, 10, 11, 12, 13, 14, 15, 16 or 17 amino acids of a MYH protein wherein said contiguous span contains at least one amino acid variants according to the present invention.

In the isolated MYH oligonucleotides containing a nucleotide variant according to the present invention, the nucleotide variant can be located in any position. In one embodiment, a nucleotide variant is at the 5' or 3' end of the oligonucleotides. In a more preferred embodiment, a MYH oligonucleotide contains only one nucleotide variant according to the present invention, which is located at the 3' end of the oligonucleotide. In another embodiment, a nucleotide variant of the present invention is located within no greater than four (4), preferably no greater than three (3), and more preferably no greater than two (2) nucleotides of the center of the oligonucleotide of the present invention. In more preferred embodiment, a nucleotide variant is located at the center or within one (1) nucleotide of the center of the oligonucleotide. For purposes of defining the location of a nucleotide variant in an oligonucleotide, the center nucleotide of an oligonucleotide with an odd number of nucleotides is considered to be the center. For an oligonucleotide with an even number of nucleotides, the bond between the two center nucleotides is considered to be the center.

Primers suitable for inclusion in the kit of the invention include any one or more of those primers as described herein.

In a preferred kit of the invention there is provided a plurality of the above PCR primers wherein multiple variations can be screened simultaneously. In an alternative embodiment of the invention DNA chip technology is used and a plurality of the aforementioned nucleic acid molecules are immobilised on a solid support.

It is within the scope of the invention to use other nucleotide detection methods such as single amplification methods being pioneered in nanotechnology (such as Q-dots). Also, single molecule detection methods can be employed (such as STM) and in either instance suitable reagents may be provided for carrying out the screening method of the invention.

Advantageously, the kit of the invention may comprise molecules that are tagged with suitable markers such as antibodies, sugars and lipids or other proteins or chemical compounds or, indeed, any means that confers upon the relevant nucleic acid or polypeptide a physical characteristic that enables the presence of the variant of the invention to be identified.

The oligonucleotides of the present invention can have a detectable marker selected from, e.g., radioisotopes, fluorescent compounds, enzymes, or enzyme co-factors operably linked to the oligonucleotide. The oligonucleotides of the present invention can be useful in genotyping as will be apparent from the description below.

In addition, the present invention also provides DNA microchips or microarray incorporating a variant MYH genomic DNA or cDNA or mRNA or an oligonucleotide according to the present invention. The microchip will allow rapid genotyping and/or haplotyping in a large scale.

As is known in the art, in microchips, a large number of different nucleic acid probes are attached or immobilized in an array on a solid support, e.g., a silicon chip or glass slide. Target nucleic acid sequences to be analyzed can be contacted with the immobilized oligonucleotide probes on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet.,14:441-447 (1996); Saiki et al., Proc. Natl. Acad. Sci. USA, 86:6230-6234 (1989); Gingeras et al., Genome Res., 8:435-448 (1998). The microchip technologies combined with computerized analysis tools allow large-scale high throughput screening. See, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996); Lockhart et al., Nat. Genet., 14:675-680 (1996); Drobyshev et al., Gene, 188:45-52 (1997).

Proteins and Polypeptides

The present invention also provides isolated proteins encoded by one of the isolated nucleic acids according to the present invention. In one aspect, the present invention provides an isolated MYH protein encoded by one of the novel MYH gene variants according to the present invention. Thus, for example, the present invention provides an isolated MYH protein having an amino acid sequence that contains one or more amino acid variants of the invention. In another example, the isolated MYH protein of the present invention has an amino acid sequence at least 95%, preferably 97%, more preferably 99% identical to one or more of SEQ ID NO:1 through SEQ ID NO:4, wherein the amino acid sequence contains one or more of the amino acid variants of the invention.

In addition, the present invention also encompasses isolated peptides having a contiguous span of at least 6, 7, 8, 9, 10, 11, 12, 13, 15, 17, 19 or 21 or more amino acids of an isolated MYH protein of the present invention said contiguous span encompassing one or more amino acid variants of the invention. In preferred embodiments, the isolated variant MYH peptides contain no greater than 200 or 100 amino acids, and preferably no greater than 50 amino acids. In specific embodiments, the MYH polypeptides in accordance with the present invention contain one or more of the amino acid variants identified in accordance with the present invention. The peptides can be useful in preparing antibodies specific to the mutant MYH proteins provided in accordance with the present invention.

As will be apparent to an ordinarily skilled artisan, the isolated nucleic acids and isolated polypeptides of the present invention can be prepared using techniques generally known in the field of molecular biology. See generally, Sambrook et al., Molecular Cloning: A Laboratory Manual, 2nd ed., Cold Spring Harbor Laboratory, Cold Spring Harbor, N.Y., 1989. The isolated MYH gene or cDNA or oligonucleotides of this invention can be operably linked to one or more other DNA fragments. For example, the isolated MYH nucleic acid (e.g., cDNA or oligonucleotides) can be ligated to another DNA such that a fusion protein can be encoded by the ligation product. The isolated MYH nucleic acid (e.g., cDNA or oligonucleotides) can also be incorporated into a DNA vector for purposes of, e.g., amplifying the nucleic acid or a portion thereof, and/or expressing a mutant MYH polypeptide or a fusion protein thereof.

Thus, the present invention also provides a vector construct containing an isolated nucleic acid of the present invention, such as a mutant MYH nucleic acid (e.g., cDNA or oligonucleotides) of the present invention. Generally, the vector construct may include a promoter operably linked to a DNA of interest (including a full-length sequence or a fragment thereof in the 5' to 3' direction or in the reverse direction for purposes of producing antisense nucleic acids), an origin of DNA replication for the replication of the vector in host cells and a replication origin for the amplification of the vector in, e.g., E. coli, and selection marker(s) for selecting and maintaining only those host cells harboring the vector. Additionally, the vector preferably also contains inducible elements, which function to control the expression of the isolated gene sequence. Other regulatory sequences such as transcriptional termination sequences and translation regulation sequences (e.g., Shine-Dalgarno sequence) can also be included. An epitope tag-coding sequence for detection and/or purification of the encoded polypeptide can also be incorporated into the vector construct. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vector construct can be introduced into the host cells or organisms by any techniques known in the art, e.g., by direct DNA transformation, microinjection, electroporation, viral infection, lipofection, gene gun, and the like. The vector construct can be maintained in host cells in an extrachromosomal state, i.e., as self-replicating plasmids or viruses. Alternatively, the vector construct can be integrated into chromosomes of the host cells by conventional techniques such as selection of stable cell lines or site-specific recombination. The vector construct can be designed to be suitable for expression in various host cells, including but not limited to bacteria, yeast cells, plant cells, insect cells, and mammalian and human cells. A skilled artisan will recognize that the designs of the vectors can vary with the host cell used.

Antibodies

The present invention also provides antibodies selectively immunoreactive with a variant MYH protein or peptide provided in accordance with the present invention and methods for making the antibodies. As used herein, the term "antibody" encompasses both monoclonal and polyclonal antibodies that fall within any antibody classes, e.g., IgG, IgM, IgA, etc. The term "antibody" also means antibody fragments including, but not limited to, Fab and F(ab')2, conjugates of such fragments, and single-chain antibodies that can be made in accordance with U.S. Pat. No. 4,704,692, which is incorporated herein by reference. Specifically, the phrase "selectively immunoreactive with one or more of the newly discovered variant MYH protein variants" as used herein means that the immunoreactivity of an antibody with a protein variant of the present invention is substantially higher than that with the MYH protein heretofore known in the art such that the binding of the antibody to the protein variant of the present invention is readily distinguishable, based on the strength of the binding affinities, from the binding of the antibody to the MYH protein having a reference amino acid sequence. Preferably, the binding constant differs by a magnitude of at least 2 fold, more preferably at least 5 fold, even more preferably at least 10 fold, and most preferably at least 100 fold.

To make such an antibody, a variant MYH protein or a peptide of the present invention having a particular amino acid variant (e.g., substitution or insertion or deletion) is provided and used to immunize an animal. The variant MYH protein or peptide variant can be made by any methods known in the art, e.g., by recombinant expression or chemical synthesis. To increase the specificity of the antibody, a shorter peptide containing an amino acid variant is preferably generated and used as antigen. Techniques for immunizing animals for the purpose of making polyclonal antibodies are generally known in the art. See Harlow and Lane, Antibodies: A Laboratory Manual, Cold Spring Harbor Laboratory, Cold Spring Harbor, N.Y., 1988. A carrier may be necessary to increase the immunogenicity of the polypetide. Suitable carriers known in the art include, but are not limited to, liposome, macromolecular protein or polysaccharide, or combination thereof. Preferably, the carrier has a molecular weight in the range of about 10,000 to 1,000,000. The polypeptide may also be administered along with an adjuvant, e.g., complete Freund's adjuvant.

The antibodies of the present invention preferably are monoclonal. Such monoclonal antibodies may be developed using any conventional techniques known in the art. For example, the popular hybridoma method disclosed in Kohler and Milstein, Nature, 256:495-497 (1975) is now a well-developed technique that can be used in the present invention. See U.S. Pat. No. 4,376,110, which is incorporated herein by reference. Essentially, B-lymphocytes producing a polyclonal antibody against a protein variant of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, Antibodies: A Laboratory Manual, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein or peptide variant of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, Nature, 312:597 (1984); Morrison, Science, 229:1202 (1985); Oi et al., Bio-Techniques, 4:214 (1986); and Wood et al., Nature, 314:446-449 (1985), all of which are incorporated herein by reference. Antibody fragments such as Fv fragments, single-chain Fv fragments (scFv), Fab' fragments, and F(ab')2 fragments can also be recombinantly produced by methods disclosed in, e.g., U.S. Pat. No. 4,946,778; Skerra & Pluckthun, Science, 240:1038-1041(1988); Better et al., Science, 240:1041-1043 (1988); and Bird, et al., Science, 242:423-426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, Adv. Immunol., 44:65-92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., Nat. Genetics, 7: 13-21 (1994); and Lonberg et al., Nature 368: 856-859 (1994), all of which are incorporated herein by reference. The transgenic non-human host animal may be immunized with suitable antigens such as a protein variant of the present invention to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library which is subsequently screened for clones encoding humanized antibodies with desired binding specificities.

Methods of Detecting MYH Variants

The present invention also provides a method for genotyping the MYH gene by determining whether an individual has a nucleotide variant or amino acid variant of the present invention.

Similarly, a method for haplotyping the MYH gene is also provided. Haplotyping can be done by any methods known in the art. For example, only one copy of the MYH gene can be isolated from an individual and the nucleotide at each of the variant positions is determined. Alternatively, an allele specific PCR or a similar method can be used to amplify only one copy of the MYH gene in an individual, and the SNPs at the variant positions of the present invention are determined. The Clark method known in the art can also be employed for haplotyping. A high throughput molecular haplotyping method is also disclosed in Tost et al., Nucleic Acids Res., 30(19):e96(2002), which is incorporated herein by reference.

Thus, additional variant(s) that are in linkage disequilibrium with the variants and/or haplotypes of the present invention can be identified by a haplotyping method known in the art, as will be apparent to a skilled artisan in the field of genetics and haplotying. The additional variants that are in linkage disequilibrium with a variant or haplotype of the present invention can also be useful in the various applications as described below.

For purposes of genotyping and haplotyping, both genomic DNA and mRNA/cDNA can be used, and both are herein referred to generically as "gene." Numerous techniques for detecting nucleotide variants are known in the art and can all be used for the method of this invention. The techniques can be protein-based or DNA-based. In either case, the techniques used must be sufficiently sensitive so as to accurately detect the small nucleotide or amino acid variations. Very often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977).

In a DNA-based detection method, target DNA sample, i.e., a sample containing MYH genomic DNA or cDNA or mRNA must be obtained from the individual to be tested. Any tissue or cell sample containing the MYH genomic DNA, mRNA, or cDNA or a portion thereof can be used. For this purpose, a tissue sample containing cell nucleus and thus genomic DNA can be obtained from the individual. Blood samples can also be useful except that only white blood cells and other lymphocytes have cell nucleus, while red blood cells are anucleus and contain only mRNA. Nevertheless, mRNA is also useful as it can be analyzed for the presence of nucleotide variants in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of a particular nucleotide variant, one technique is simply sequencing the target genomic DNA or cDNA, particularly the region encompassing the nucleotide variant locus to be detected. Various sequencing techniques are generally known and widely used in the art including the Sanger method and Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and thus can also be used in the present invention. See Nordstrom et al., Biotechnol. Appl. Biochem., 31(2):107-112 (2000); Ahmadian et al., Anal. Biochem., 280: 103-110 (2000).

Alternatively, the restriction fragment length polymorphism (RFLP) and AFLP method may also prove to be useful techniques. In particular, if a nucleotide variant in the target MYH DNA results in the elimination or creation of a restriction enzyme recognition site, then digestion of the target DNA with that particular restriction enzyme will generate an altered restriction fragment length pattern. Thus, a detected RFLP or AFLP will indicate the presence of a particular nucleotide variant.

Another useful approach is the single-stranded conformation polymorphism assay (SSCA), which is based on the altered mobility of a single-stranded target DNA spanning the nucleotide variant of interest. A single nucleotide change in the target sequence can result in different intramolecular base pairing pattern, and thus different secondary structure of the single-stranded DNA, which can be detected in a non-denaturing gel. See Orita et al., Proc. Natl. Acad. Sci. USA, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., Biotechniques, 5:1016-24 (1999); Sheffield et al., Am. J. Hum, Genet., 49:699-706 (1991); Wartell et al., Nucleic Acids Res., 18:2699-2705 (1990); and Sheffield et al., Proc. Natl. Acad. Sci. USA, 86:232-236 (1989). In addition, the double-strand conformation analysis (DSCA) can also be useful in the present invention. See Arguello et al., Nat. Genet., 18:192-194 (1998).

The presence or absence of a nucleotide variant at a particular locus in the MYH gene of an individual can also be detected using the amplification refractory mutation system (ARMS) technique. See e.g., European Patent No. 0,332,435; Newton et al., Nucleic Acids Res., 17:2503-2515 (1989); Fox et al., Br. J. Cancer, 77:1267-1274 (1998); Robertson et al., Eur. Respir. J., 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., Clin. Chem. 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., Genomics, 8:684-692 (1990); Shumaker et al., Hum. Mutat., 7:346-354 (1996); Chen et al., Genome Res., 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., Science, 241:1077-1080 (1988); Chen et al, Genome Res., 8:549-556 (1998); Iannone et al., Cytometry, 39:131-140 (2000). Thus, for example, to detect a single-nucleotide mutation at a particular locus in the MYH gene, two oligonucleotides can be synthesized, one having the MYH sequence just 5' upstream from the locus with its 3' end nucleotide being identical to the nucleotide in the variant locus of the MYH gene, the other having a nucleotide sequence matching the MYH sequence immediately 3' downstream from the locus in the MYH gene. The oligonucleotides can be labeled for the purpose of detection. Upon hybridizing to the target MYH gene under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., Proc. Nati. Acad. Sci. USA, 80:278-282 (1983); Saiki et al, Proc. Natl. Acad. Sci. USA, 86:6230-6234 (1989). Oligonucleotide probes (allele-specific) hybridizing specifically to a MYH gene allele having a particular gene variant at a particular locus but not to other alleles can be designed by methods known in the art. The probes can have a length of, e.g., from 10 to about 50 nucleotide bases. The target MYH DNA and the oligonucleotide probe can be contacted with each other under conditions sufficiently stringent such that the nucleotide variant can be distinguished from the wild-type MYH gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular nucleotide variant.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, Human Genetics, 42:726 (1988). Alternatively, in a RNase protection assay, a RNA probe can be prepared spanning the nucleotide variant site to be detected and having a detection marker. See Giunta et al., Diagn. Mol. Path., 5:265-270 (1996); Finkelstein et al., Genomics, 7:167-172 (1990); Kinszler et al., Science 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., Nucleic Acids Res., 25:3377-3378 (1997).

In the mutS assay, a probe can be prepared matching the MYH gene sequence surrounding the locus at which the presence or absence of a mutation is to be detected, except that a predetermined nucleotide is used at the variant locus. Upon annealing the probe to the target DNA to form a duplex, the *E. coli* mutS protein is contacted with the duplex. Since the mutS protein binds only to heteroduplex sequences containing a nucleotide mismatch, the binding of the mutS protein will be indicative of the presence of a mutation. See Modrich et al., Ann. Rev. Genet., 25:229-253 (1991).

A great variety of improvements and variations have been developed in the art on the basis of the above-described basic techniques, and can all be useful in detecting mutations or nucleotide variants in the present invention. For example, the "sunrise probes" or "molecular beacons" utilize the fluorescence resonance energy transfer (FRET) property and give rise to high sensitivity. See Wolf et al., Proc. Nat. Acad. Sci. USA, 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., Nucleic Acids Res., 25:2516-2521 (1997); Rychlik et al., Nucleic Acids Res., 17:8543-8551 (1989); Sharkey et al., Bio/Technology 12:506-509 (1994); Tyagi et al., Nat. Biotechnol., 14:303-308 (1996); Tyagi et al., Nat. Biotechnol., 16:49-53 (1998). The homo-tag assisted non-dimer system (HANDS) can be used in combination with the molecular beacon methods to suppress primer-dimer accumulation. See Brownie et al., Nucleic Acids Res., 25:3235-3241 (1997).

Dye-labeled oligonucleotide ligation assay is a FRET-based method, which combines the OLA assay and PCR. See Chen et al., Genome Res. 8:549-556 (1998). TaqMan is another FRET-based method for detecting nucleotide variants. A TaqMan probe can be oligonucleotides designed to have the nucleotide sequence of the MYH gene spanning the variant locus of interest and to differentially hybridize with different MYH alleles. The two ends of the probe are labeled with a quenching fluorophore and a reporter fluorophore, respectively. The TaqMan probe is incorporated into a PCR reaction for the amplification of a target MYH gene region containing the locus of interest using Taq polymerase. As Taq polymerase exhibits 5'-3' exonuclease activity but has no 3'-5' exonuclease activity, if the TaqMan probe is annealed to the target MYH DNA template, the 5'-end of the TaqMan probe will be degraded by Taq polymerase during the PCR reaction thus separating the reporting fluorophore from the quenching fluorophore and releasing fluorescence signals. See Holland et al., Proc. Natl. Acad. Sci. USA, 88:7276-7280 (1991); Kalinina et al., Nucleic Acids Res., 25:1999-2004 (1997); Whitcombe et al., Clin. Chem., 44:918-923 (1998).

In addition, the detection in the present invention can also employ a chemiluminescence-based technique. For example, an oligonucleotide probe can be designed to hybridize to either the wild-type or a variant MYH gene locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., Nucleic Acids Res., 24:4998-5003 (1996).

The detection of genetic variation in the MYH gene in accordance with the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., Electrophoresis, 20:1171-1176 (1999).

Another useful technique that is gaining increased popularity is mass spectrometry. See Graber et al., Curr. Opin. Biotechnol., 9:14-18 (1998). For example, in the primer oligo base extension (PROBETM) method, a target nucleic acid is immobilized to a solid-phase support. A primer is annealed to the target immediately 5' upstream from the locus to be analyzed. Primer extension is carried out in the presence of a selected mixture of deoxyribonucelotides and dideoxyribonucleotides. The resulting mixture of newly extended primers is then analyzed by MALDI-TOF. See e.g., Monforte et al., Nat. Med., 3:360-362 (1997).

In addition, the microchip or microarray technologies are also applicable to the detection method of the present invention. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet.,14:441-447 (1996); Saiki et al., Proc. Natl. Acad. Sci. USA, 86:6230-6234 (1989); Gingeras et al., Genome Res., 8:435-448 (1998). Alternatively, the multiple target nucleic acid sequences to be studied are fixed onto a substrate and an array of probes is contacted with the immobilized target sequences. See Drmanac et al., Nat. Biotechnol., 16:54-58 (1998). Numerous microchip technologies have been developed incorporating one or more of the above described techniques for detecting mutations. The microchip technologies combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996); Lockhart et al., Nat. Genet., 14:675-680 (1996); Drobyshev et al., Gene, 188:45-52 (1997).

As is apparent from the above survey of the suitable detection techniques, it may or may not be necessary to amplify the target DNA, i.e., the MYH gene or cDNA or mRNA to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., Molecular Cloning: A Laboratory Manual, 2nd ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., J. Clin. Microbiol., 34:901-907 (1996); Collins et al., Nucleic Acids Res., 25:2979-2984 (1997); Horn et al., Nucleic Acids Res., 25:4835-4841 (1997); Horn et al., Nucleic Acids Res., 25:4842-4849 (1997); Nilsen et al., J. Theor. Biol., 187:273-284 (1997).

In yet another technique for detecting single nucleotide variations, the Invader® assay utilizes a novel linear signal amplification technology that improves upon the long turn-around times required of the typical PCR DNA sequenced-based analysis. See Cooksey et al., Antimicrobial Agents and Chemotherapy 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader® system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., Nat. Biotechnol., 17:292-296 (1999).

The rolling circle method is another method that avoids exponential amplification. Lizardi et al., Nature Genetics, 19:225-232 (1998) (which is incorporated herein by reference). For example, Sniper™, a commercial embodiment of this method, is a sensitive, high-throughput SNP scoring system designed for the accurate fluorescent detection of specific variants. For each nucleotide variant, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, Life Science News 6, 2000, Amersham Pharmacia Biotech (2000). A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., Anal. Chem., 69:4703-4707 (1997). The fluorescence correlation spectroscopy is based on the spatio-temporal correlations among fluctuating light signals and trapping single molecules in an electric field. See Eigen et al., Proc. Natl. Acad. Sci. USA, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., Anal. Chem., 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a nucleotide variant in the MYH gene of a particular individual should be apparent to a skilled artisan apprised of this disclosure.

Protein-based detection techniques may also prove to be useful, especially when the nucleotide variant causes amino acid substitutions or deletions or insertions or frameshift that affect the protein primary, secondary or tertiary structure. To detect the amino acid variations, protein sequencing techniques may be used. For example, an MYH protein or fragment thereof can be synthesized by recombinant expression using an MYH DNA fragment isolated from an individual to be tested. Preferably, an MYH cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., Anal. Chem., 72:757-763 (2000).

Other useful protein-based detection techniques include immunoaffinity assays based on antibodies selectively immunoreactive with mutant MYH proteins according to the present invention. The method for producing such antibodies is described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

Accordingly, the presence or absence of an MYH nucleotide variant or amino acid variant in an individual can be determined using any of the detection methods described above.

Typically, once the presence or absence of an MYH nucleotide variant or an amino acid variant resulting from a nucleotide variant of the present invention is determined, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to the presence or absence of a MYH nucleotide variant of the present invention in the individual tested can be embodied in descriptive statements, diagrams, photographs, charts, images or any other visual forms. For example, images of gel electrophoresis of PCR products can be used in explaining the results. Diagrams showing where a variant occurs in an individual's MYH gene are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of a nucleotide variant or amino acid variant of the present invention in the individual tested can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present invention also encompasses a method for producing a transmittable form of information on the MYH genotype of an individual. The method comprises the steps of (1) determining the presence or absence of a nucleotide variant according to the present invention in the MYH gene of the individual; and (2) embodying the result of the determining step in a transmittable form. The transmittable form is the product of the production method.

Kits

In some embodiments, the present invention also provides a kit for genotyping MYH gene, i.e., determining the presence or absence of one or more of the nucleotide or amino acid variants of present invention in a MYH gene in a sample obtained from a patient. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting nucleotide or amino acid variants discovered in accordance with the present invention using the above-discussed detection techniques.

In one embodiment, the detection kit includes one or more oligonucleotides useful in detecting one or more of the nucleotide variants in MYH gene. Preferably, the oligonucleotides are allele-specific, i.e., are designed such that they hybridize only to a mutant MYH gene containing a particular nucleotide variant discovered in accordance with the present invention, under stringent conditions. Thus, the oligonucleotides can be used in mutation-detecting techniques such as allele-specific oligonucleotides (ASO), allele-specific PCR, Taq-Man, chemiluminescence-based techniques, molecular beacons, and improvements or derivatives thereof, e.g., microchip technologies. The oligonucleotides in this embodiment preferably have a nucleotide sequence that matches a nucleotide sequence of a variant MYH gene allele containing a nucleotide variant to be detected. The length of the oligonucleotides in accordance with this embodiment of the invention can vary depending on its nucleotide sequence and the hybridization conditions employed in the detection procedure. Preferably, the oligonucleotides contain from about 10 nucleotides to about 100 nucleotides, more preferably from about 15 to about 75 nucleotides, e.g., contiguous span of 18, 19, 20, 21, 22, 23, 24 or 25 to 21, 22, 23, 24, 26, 27, 28, 29 or 30 nucleotide residues of a MYH nucleic acid one or more of the residues being a nucleotide variant of the present invention. Under most conditions, a length of 18 to 30 may be optimum. In any event, the oligonucleotides should be designed such that it can be used in distinguishing one nucleotide variant from another at a particular locus under predetermined stringent hybridization conditions. Preferably, a nucleotide variant is located at the center or within one (1) nucleotide of the center of the oligonucleotides, or at the 3' or 5' end of the oligonucleotides. The hybridization of an oligonucleotide with a nucleic acid and the optimization of the length and hybridization conditions should be apparent to a person of skill in the art. See generally, Sambrook et al., Molecular Cloning: A Laboratory Manual, 2nd ed., Cold Spring Harbor Laboratory, Cold Spring Harbor, N.Y., 1989. Notably, the oligonucleotides in accordance with this embodiment are also useful in mismatch-based detection techniques described above, such as electrophoretic mobility shift assay, RNase protection assay, mutS assay, etc.

In another embodiment of this invention, the kit includes one or more oligonucleotides suitable for use in detecting techniques such as ARMS, oligonucleotide ligation assay (OLA), and the like. The oligonucleotides in this embodiment include a MYH gene sequence of about 10 to about 100 nucleotides, preferably from about 15 to about 75 nucleotides, e.g., contiguous span of 18, 19, 20, 21, 22, 23, 24 or 25 to 21, 22, 23, 24, 26, 27, 28, 29 or 30 nucleotide residues immediately 5' upstream from the nucleotide variant to be analyzed. The 3' end nucleotide in such oligonucleotides is a nucleotide variant in accordance with this invention.

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with certain MYH proteins or polypeptides containing specific amino acid variants discovered in the present invention. Methods for producing and using such antibodies have been described above in detail.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit preferably includes instructions on using the kit for detecting nucleotide variants in MYH gene sequences.

The present invention further relates to methods of determining in and individual predisposition to cancer, especially colorectal cancer. As indicated above, the present invention provides MYH polymorphisms associated with cancer, especially colorectal cancer. Thus, the polymorphisms disclosed herein are particularly useful in predicting predisposition to cancer in an individual.

Thus, in one aspect, the present invention encompasses a method for predicting or detecting cancer susceptibility in an individual, which comprises the step of genotyping the individual to determine the individual's genotype at one or more of the loci identified in the present invention, or another locus at which the genotype is in linkage disequilibrium with one of the polymorphisms of the present invention. Thus, if one or more of the polymorphisms of the invention is detected then it can be reasonably predicted that the individual is at an increased risk of developing cancer, particularly colon cancer.

Methods for Screening for Therapeutics

The present invention further provides a method for identifying compounds for treating or preventing symptoms amendable to treatment by alteration of MYH protein activities. For this purpose, variant MYH protein or fragment thereof containing a particular amino acid variant in accordance with the present invention can be used in any of a variety of drug screening techniques. Drug screening can be performed as described herein or using well known techniques, such as those described in U.S. Pat. Nos. 5,800,998 and 5,891,628, both of which are incorporated herein by reference. The candidate therapeutic compounds may include, but are not limited to proteins, small peptides, nucleic acids, and analogs thereof. Preferably, the compounds are small organic molecules having a molecular weight of no greater than 10,000 dalton, more preferably less than 5,000 dalton.

In one embodiment of the present invention, the method is primarily based on binding affinities to screen for compounds capable of interacting with or binding to a MYH protein containing one or more amino acid variants of the invention.

Compounds to be screened may be peptides or derivatives or mimetics thereof, or non-peptide small molecules. Conveniently, commercially available combinatorial libraries of compounds or phage display libraries displaying random peptides are used.

Various screening techniques known in the art may be used in the present invention. The MYH protein variants (drug target) can be prepared by any suitable methods, e.g., by recombinant expression and purification. The polypeptide or fragment thereof may be free in solution but preferably is immobilized on a solid support, e.g., in a protein microchip, or on a cell surface. Various techniques for immobilizing proteins on a solid support are known in the art. For example, PCT Publication WO 84/03564 discloses synthesizing a large numbers of small peptide test compounds on a solid substrate, such as plastic pins or other surfaces. Alternatively, purified mutant MYH protein or fragment thereof can be coated directly onto plates such as multi-well plates. Non-neutralizing antibodies, i.e., antibodies capable binding to the MYH protein or fragment thereof but do not substantially affect its biological activities may also be used for immobilizing the MYH protein or fragment thereof on a solid support. To effect the screening, test compounds can be contacted with the immobilized MYH protein or fragment thereof to allow binding to occur to form complexes under standard binding assays. Either the drug target or test compounds are labeled with a detectable marker using well known labeling techniques. To identify binding compounds, one may measure the formation of the drug target-test compound complexes or kinetics for the formation thereof.

Alternatively, a known ligand capable of binding to the drug target can be used in competitive binding assays. Complexes between the known ligand and the drug target can be formed and then contacted with test compounds. The ability of a test compound to interfere with the interaction between the drug target and the known ligand is measured using known techniques. One exemplary ligand is an antibody capable of specifically binding the drug target. Particularly, such an antibody is especially useful for identifying peptides that share one or more antigenic determinants of the MYH protein or fragment thereof.

In another embodiment, a yeast two-hybrid system may be employed to screen for proteins or small peptides capable of interacting with a MYH protein variant. For example, a battery of fusion proteins each contains a random small peptide fused to e.g., Gal 4 activation domain, can be co-expressed in yeast cells with a fusion protein having the Gal 4 binding domain fused to a MYH protein variant. In this manner, small peptides capable of interacting with the MYH protein variant can be identified. Alternatively, compounds can also be tested in a yeast two-hybrid system to determine their ability to inhibit the interaction between the MYH protein variant and a known protein capable of interacting with the MYH protein or polypeptide or fragment thereof. Again, one example of such proteins is an antibody specifically against the MYH protein variant. Yeast two-hybrid systems and use thereof are generally known in the art and are disclosed in, e.g., Bartel et al., in: Cellular Interactions in Development: A Practical Approach, Oxford University Press, pp. 153-179 (1993); Fields and Song, Nature, 340:245-246 (1989); Chevray and Nathans, Proc. Natl. Acad. Sci. USA, 89:5789-5793 (1992); Lee et al., Science, 268:836-844 (1995); and U.S. Pat. Nos. 6,057,101, 6,051,381, and 5,525,490, all of which are incorporated herein by reference.

The compounds thus identified can be further tested for activities, e.g., in stimulating the variant MYH's biological activities, e.g., in DNA mismatch repair. Once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., Bio/Technology, 9:19-21 (1991); U.S. Pat. Nos. 5,800,998 and 5,891,628, all of which are incorporated herein by reference. An example of rational drug design is the development of HIV protease inhibitors. See Erickson et al., Science, 249: 527-533 (1990). Preferably, rational drug design is based on one or more compounds selectively binding to a variant MYH protein or a fragment thereof.

In one embodiment, the three-dimensional structure of, e.g., a MYH protein variant, is determined by biophysics techniques such as X-ray crystallography, computer modeling, or both. Desirably, the structure of the complex between an effective compound and the variant MYH protein is determined, and the structural relationship between the compound and the protein is elucidated. In this manner, the moieties and the three-dimensional structure of the selected compound, i.e., lead compound, critical to the its binding to the variant MYH protein are revealed. Medicinal chemists can then design analog compounds having similar moieties and structures. In addition, the three-dimensional structure of wild-type MYH protein is also desirably deciphered and compared to that of a variant MYH protein. This will aid in designing compounds selectively interacting with the variant MYH protein.

In another approach, a selected peptide compound capable of binding the MYH protein variant can be analyzed by an alanine scan. See Wells, et al., Methods Enzymol., 202:301-306 (1991). In this technique, an amino acid residue of the peptide is replaced by Alanine, and its effect on the peptide's binding affinity to the variant MYH protein is tested. Amino acid residues of the selected peptide are analyzed in this manner to determine the domains or residues of the peptide important to its binding to variant MYH protein. These residues or domains constituting the active region of the compound are known as its "pharmacophore." This information can be very helpful in rationally designing improved compounds.

Once the pharmacophore has been elucidated, a structural model can be established by a modeling process which may include analyzing the physical properties of the pharmacophore such as stereochemistry, charge, bonding, and size using data from a range of sources, e.g., NMR analysis, x-ray diffraction data, alanine scanning, and spectroscopic techniques and the like. Various techniques including computational analysis, similarity mapping and the like can all be used in this modeling process. See e.g., Perry et al., in OSAR: Quantitative Structure-Activity Relationships in Drug Design, pp. 189-193, Alan R. Liss, Inc., 1989; Rotivinen et al., Acta Pharmaceutical Fennica, 97:159-166 (1988); Lewis et al., Proc. R. Soc. Lond., 236:125-140 (1989); McKinaly et al., Annu. Rev. Pharmacol. Toxiciol., 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed.

Cell Lines and Transgenic Animals

In yet another aspect of the present invention, a cell line and a transgenic animal carrying an MYH gene containing one or more of the nucleotide variants in accordance with the present invention are provided. The cell line and transgenic animal can be used as a model system for studying cancers and testing various therapeutic approaches in treating cancers.

To establish the cell line, cells expressing the variant MYH protein can be isolated from an individual carrying the nucleotide variants. The primary cells can be transformed or immortalized using techniques known in the art. Alternatively, normal cells expressing a wild-type MYH protein or other type of nucleotide variants can be manipulated to replace the entire endogenous MYH gene with a variant MYH gene containing one or more of the nucleotide variants in accordance with the present invention, or simply to introduce mutations into the endogenous MYH gene. The genetically engineered cells can further be immortalized.

A more valuable model system is a transgenic animal. A transgenic animal can be made by replacing the endogenous animal MYH gene with a variant MYH gene containing one or more of the nucleotide variants in accordance with the present invention. Alternatively, insertions and/or deletions can be introduced into the endogenous animal MYH gene to simulate the MYH alleles discovered in accordance with the present invention. Techniques for making such transgenic animals are well known and are described in, e.g., Capecchi, et al., Science, 244:1288 (1989); Hasty et al., Nature, 350:243 (1991); Shinkai et al., Cell, 68:855 (1992); Mombaerts et al., Cell, 68:869 (1992); Philpott et al., Science, 256:1448 (1992); Snouwaert et al., Science, 257:1083 (1992); Donehower et al., Nature, 356:215 (1992); Hogan et al., Manipulating the Mouse Embryo; A Laboratory Manual, 2nd edition, Cold Spring Harbor Laboratory Press, 1994; and U.S. Pat. Nos. 5,800,998, 5,891,628, and 4,873,191, all of which are incorporated herein by reference.

The cell line and transgenic animal are valuable tools for studying the variant MYH genes, and in particular for testing in vivo the compounds identified in the screening method of this invention and other therapeutic approaches as discussed below. As is known in the art, studying drug candidates in a suitable animal model before advancing them into human clinical trials is particularly important because efficacy of the drug candidates can be confirmed in the model animal, and the toxicology profiles, side effects, and dosage ranges can be determined. Such information is then used to guide human clinical trials.

EXAMPLES

The basis for the invention will now be described in more detail with reference to the following Examples and Tables, in which:

Example 1 describes the methods for analysing MYH.

Example 2 describes the identification of MYH-deficient patients and four novel MYH mutations.

Table 1 shows the primers used for amplification of MYH;

Table 2 shows the regional polyposis registers and MYH polyposis families;

Table 3 shows the mutations of phenotypes in 25 MYH polyposis index cases.

Example 1

Methods and Protocols Relating to the Dentification of Novel MYH Mutations samples Nucleic acid was prepared from venous blood samples using standard methods.

PCR amplification

Exons 1-16 of MYH (Table 1) were amplified as 16 fragments. Standard PCR was carried out in 50 µl reaction volumes containing 100 ng genomic DNA, 25 pmole primers, 0.2 mM dNTPs, 5 µl reaction buffer and 1U AmpliTaq Gold DNA Polymerase (Applied Biosystems). Cycling parameters were 94° C. 10 mins, followed by 32 cycles of 50-67° C. 1 min, 72° C. 1 min, 94° C. 30 secs, and a final step of 72° C. 10 mins.

TABLE 1

Primers used for the amplification of MYH

| Exon | Primer name | SEQ ID NOs | Sequence | Product size | Annealing Temp. |
|---|---|---|---|---|---|
| 1 | Y1F | 5 | 5'-GAAGCTGCGGGAGCTGAAA-3' | 133 bp | 460° C. |
|   | Y1R | 6 | 5'-ATCCCCGACTGCCTGAACC-3' |   |   |
| 2 | Y2F | 7 | 5'-CTGCATTTGGCTGGGTCTTT-3' | 263 bp | 54° C. |
|   | Y2R | 8 | 5'-CGCACCTGGCCCTTAGTAAG-3' |   |   |
| 3 | Y3F | 9 | 5'-AGCCTGTGCAGGGATGATTG-3' | 272 bp | 57° C. |
|   | Y3R | 10 | 5'-CAACCCCAGATGAGGAGTTAGG-3' |   |   |
| 4 | Y4F | 11 | 5'-CTCATCTGGGGTTGCATTGA-3' | 167 bp | 57° C. |
|   | Y4R | 12 | 5'-GGGTTGGCATGAGGACACTG-3' |   |   |
| 5 | Y5F | 13 | 5'-GGGCAGGTCAGCAGTGTC-3' | 189 bp | 57° C. |
|   | Y5R | 14 | 5'-TACACCCACCCCAAAGTAGA-3' |   |   |

TABLE 1-continued

Primers used for the amplification of MYH

| Exon | Primer name | SEQ ID NOs | Sequence | Product size | Annealing Temp. |
|---|---|---|---|---|---|
| 6 | Y6F | 15 | 5'-TACTTTGGGGTGGGTGTAGA-3' | 185 bp | 54° C. |
|   | Y6R | 16 | 5'-AAGAGATCACCCGTCAGTCC-3' | | |
| 7 | Y7F | 17 | 5'-GGGACTGACGGGTGATCTCT-3' | 186 bp | 54° C. |
|   | Y7R | 18 | 5'-TTGGAGTGCAAGACTCAAGATT-3' | | |
| 8 | Y8F | 19 | 5'-CCAGGAGTCTTGGGTGTCTT-3' | 240 bp | 57° C. |
|   | Y8R | 20 | 5'-AGAGGGGCCAAAGAGTTAGC-3' | | |
| 9 | Y9F | 21 | 5'-AACTCTTTGGCCCCTCTGTG-3' | 196 bp | 57° C. |
|   | Y9R | 22 | 5'-GAAGGGAACACTGCTGTGAAG-3' | | |
| 10 | Y10F | 23 | 5'-GTGCTTCAGGGGTGTCTGC-3' | 262 bp | 57° C. |
|   | Y10R | 24 | 5'-TGTCATAGGGCAGAGTCACTCC-3' | | |
| 11 | Y11F | 25 | 5'-TAAGGAGTGACTCTGCCCTATG-3' | 248 bp | 54° C. |
|   | Y11R | 26 | 5'-GCCAAGAGGGGCTTTAGG-3' | | |
| 12 | Y12F | 27 | 5'-AGCCCCTCTTGGCTTGAGTA-3' | 298 bp | 57° C. |
|   | Y12R | 28 | 5'-TGCCGATTCCCTCCATTCT-3' | | |
| 13 | Y13F | 29 | 5'-AGGGCAGTGGCATGAGTAAC-3' | 242 bp | 57° C. |
|   | Y13R | 30 | 5'-GGCTATTCCGCTGCTCACTT-3' | | |
| 14 | Y14F | 31 | 5'-TTGGCTTTTGAGGCTATATCC-3' | 256 bp | 54° C. |
|   | Y14R | 32 | 5'-CATGTAGGAAACACAAGGAAGTA-3' | | |
| 15 | Y15F | 33 | 5'-TGAAGTTAAGGGCAGAACACC-3' | 205 bp | 54° C. |
|   | Y15R | 34 | 5'-GTTCACCCAGACATTCGTTAGT-3' | | |
| 16 | Y16F | 35 | 5'-AGGACAAGGAGAGGATTCTCTG-3' | 224 bp | 54° C. |
|   | Y16R | 36 | 5'-GGAATGGGGCTTTCAGA-3' | | |

Sequencing

Standard PCR products were sequenced manually using the ThermoSequenase cycle sequencing kit (Amersham), and analysed on 6% polyacrylamide gels.

Assays for Sequence Variants in MYH

The Y165C (494 A>G) missense variant in exon 7 was assayed by direct sequencing and the G382D (1145 G>A) missense variant was assayed using a BglII digest of exon 13 PCR products.

Example 2

Identification of MYH-Deficient Patients and Four Novel MYH Mutations

We applied the following selection criteria in six well established regional polyposis registers in the United Kingdom (Table 2): 1) a family history showing no vertical transmission of polyposis 2) at least 10 colorectal adenomas with or without colorectal cancer in the index case 3) no clearly pathogenic mutation in the APC gene identified during genetic testing. We then sought MYH mutations in blood DNA samples from affected index cases. In previous reports (Al-Tassan et al. Nature Genet 2002, 30:227-232; Jones et al. Hum Mol Genet 2002, 11: 2961-7; Sieber et al. New Engl. J. Med. 2003, 348: 791-799), 31 out of 36 mutant alleles characterised in Caucasian patients with biallelic MYH mutations and colorectal polyposis were either Y165C (18 alleles) or G382D (13 alleles) while in the general Caucasian population these alleles have frequencies under 1% (Al-Tassan et al. Nature Genet 2002, 30:227-232; Sieber et al. New Engl. J. Med. 2003, 348: 791-799). Therefore, in Caucasian index cases we first assayed for these mutations by sequencing of exon 7 (for Y165C) and by BglII restriction enzyme digestion (for G382D). In cases heterozygous for either Y165C or G382D we screened for mutations affecting the second MYH allele by sequencing its 16 coding exons. Since different MYH mutations appear to be important in non-Caucasians (Jones et al. Hum Mol Genet 2002, 11: 2961-7) we sequenced all exons of MYH in all non-Caucasian index cases. All mutations were confirmed by sequencing at least two independent PCR products.

The six registers included 614 apparently unrelated families with presumptive or genetically confirmed diagnoses of FAP or AFAP. Of these, 111 fulfilled our criteria for MYH testing and had blood DNA samples available (Table 2). Biallelic MYH mutations were identified in 25 (23%), eighteen males and seven females (Table 3). Cases CF2-CF9 have been reported before (Al-Tassan et al. Nature Genet 2002, 30:227-232; Jones et al. Hum Mol Genet 2002, 11: 2961-7), and include three apparently unrelated Indian probands who were all homozygous for the E446X mutation. The seventeen previously unreported cases include a further Indian patient who is also an E466X homozygote. The four families comprised all Indian families among the 111 tested and this mutation may be an important cause of polyposis and colon cancer in the Indian population, among whom these disorders are uncommon. We identified four novel mutations in Caucasian families: Q324X (C to T at nucleotide 970), W117R (T to A at nucleotide 349), 347−1 G to A and 891+3 A to C. Three further cases were apparently heterozygotes (one for Y165C and two for G382D, with 15, 20 and "numerous" adenomas respectively). However, as sequencing of exons cannot detect all classes of pathogenic mutation, second mutations could have escaped detection.

The mean age at diagnosis of the homozygous or compound heterozygous index patients was 46 years (median 48 years, range 13-65 years). Nine were specified as having over 100 adenomas (a Pakistani case CF4 was homozygous for an early truncating mutation and had over 400), eleven had between 10 and 100 adenomas and in five the adenomas were described as being "multiple, too many to count", "numerous" or "throughout the colon". Twelve of the 25 index cases (48%) had colorectal cancer (all but one at presentation), diagnosed at a mean age of 49.7 years. Two cases had two separate primaries and two had four separate primaries. The only extra-colonic cancer was a gastric cancer diagnosed at 17 years in case M1, much the youngest of the index cases, suggesting the possibility of additional aetiological factors. Case SO1 was reported to have duodenal adenomas but no extracolonic manifestations of FAP were noted in other cases.

Among the fifty obligate heterozygote parents, two had confirmed colorectal cancers diagnosed at 71 and 73 years of age. Another had died at 71 years with hepatic metastasis from an unidentified primary. A larger series is required to address the question of possible heterozygote risk in later life. However, these data suggest that any increase is likely to be small. The index cases had a total of 64 siblings of whom 17 (27%) were known to be affected by colorectal polyposis, consistent with autosomal recessive transmission. Seven had also developed colorectal cancer at a mean age of 47.1 years.

Analysis of DNA samples available from five of the affected siblings confirmed the same mutations as the respective index cases, including one compound heterozygote for Y165C and G382D who had colon cancer and only three adenomas at 43 years of age. However, we have also screened over 40 index cases with 4-10 adenomas and did not identify any with biallelic MYH mutations (data not shown) and Sieber et al. (New Engl. J. Med. 2003, 348: 791-799) studied 152 patients with between three and one hundred adenomas but identified biallelic MYH mutations only in cases with over 15 adenomas. Therefore, this less florid phenotype appears to be associated only rarely with biallelic MYH mutation. Our data indicate that the colorectal phenotype of autosomal recessive MYH polyposis can closely resemble autosomal dominant FAP or AFAP. Indeed, at least 10 of the index cases reported here had over 100 adenomas and in several microadenomas were also noted. Previously, these features were considered pathognomonic for FAP. Genetic analysis of MYH should now be offered to patients with an FAP or AFAP-like phenotype when there is no clear evidence of vertical transmission. Predictive genetic testing should be offered to the siblings of cases found to have biallelic mutations to assess their need for endoscopic surveillance. In those found to be at risk this should be undertaken as for FAP. Further and larger studies are needed to clarify colorectal cancer risks for MYH heterozygotes and whether they require surveillance.

TABLE 2

REGIONAL POLYPOSIS REGISTERS AND MYH POLYPOSIS FAMILIES

| | Register | Health region and population | No of unrelated families on register | No of families studied for MYH mutations | No with biallelic MYH mutation | No of apparent heterozygotes |
|---|---|---|---|---|---|---|
| 1 | Birmingham | West Midlands 5.3 million | 116 | 15 | 2 | 0 |
| 2 | Cambridge | East Anglia 2.8 million | 114 | 17 | 3 | 1 |
| 3 | Cardiff | Wales 2.9 million | 108 | 29 | 10 | 1 |
| 4 | Liverpool | Mersey 2.5 million | 55 | 6 | 0 | 0 |
| 5 | Manchester | North West 4.1 million | 119 | 21 | 4 | 1 |
| 6 | Southampton | Wessex 2.6 million | 102 | 23 | 6 | 0 |

TABLE 3

MUTATIONS AND PHENOTYPES IN 25 MYH POLYPOSIS INDEX CASES

| Patient | Sex | Ethnicity | Mutation 1 | Mutation 2 | No of adenomas | Age at diagnosis | Colorectal Cancers Y/N | Other cancer Y/N |
|---|---|---|---|---|---|---|---|---|
| B1 | F | Caucasian | Y165C | Y165C | "some 10's" | 46 | Yes × 1 | No |
| B2 | F | Caucasian | G382D | 891 + 3 A→C | "multiple" | 34 | No | No |
| CB1 | M | Caucasian | Y165C | G382D | <100 | 48 | No | No |
| CB2 | M | Caucasian | G382D | G382D | ~70 | 62 | Yes × 2 | No |
| CB3 | F | Caucasian | Y165C | 347 − 1 G→A | 14 | 56 | No | No |
| CF1 | M | Caucasian | Y165C | G382D | 98 | 53 | No | No |
| CF2 | M | Indian | E466X | E466X | >100 | 65 | Yes × 2 | No |
| CF3 | M | Indian | E466X | E466X | 26* | 36 | Yes | No |
| CF4 | M | Pakistani | Y90X | Y90X | >400 | 61 | Yes × 1 | No |
| CF5 | M | Caucasian | Y165C | Y165C | >100 | 46 | No | No |
| CF6 | M | Indian | E466X | E466X | >200 | 49 | No | No |
| CF7 | F | Caucasian | Y165C | G382D | >100 | 45 | Yes × 4 | No |

TABLE 3-continued

MUTATIONS AND PHENOTYPES IN 25 MYH POLYPOSIS INDEX CASES

| Patient | Sex | Ethnicity | Mutation 1 | Mutation 2 | No of adenomas | Age at diagnosis | Colorectal Cancers Y/N | Other cancer Y/N |
|---|---|---|---|---|---|---|---|---|
| CF8 | F | Caucasian | Y165C | Y165C | >22 | 38 | Yes × 1 | No |
| CF9 | M | Caucasian | Y165C | G382D | ~50 | 59 | No | No |
| CF10 | M | Caucasian | G382D | Q324X | >30 | 40 | No | No |
| M1 | M | Caucasian | Y165C | G382D | >100 | 13 | No | Stomach cancer at 17 yrs |
| M2 | M | Indian | E466X | E466X | >100 | 52 | Yes × 1 | No |
| M3 | F | Caucasian | Y165C | Y165C | "numerous" | 45 | Yes × 1 | No |
| M4 | F | Caucasian | Y165C | G382D | >20 | 58 | Yes × 4 | No |
| SO1 | M | Caucasian | Y165C | Y165C | "100's" | 30 | Yes × 1 at 38 yrs | Duodenal polyps |
| SO2 | M | Caucasian | Y165C | G382D | "numerous" | 51 | No | No |
| SO3 | M | Caucasian | Y165C | Y165C | ~50 | 50 | Yes | No |
| SO4 | M | Caucasian | Y165C | Y165C | "multiple throughout colon" | 34 | No | No |
| SO5 | M | Caucasian | Y165C | 891 + 3 A→C | "numerous" | 48 | No | No |
| SO6 | M | Caucasian | Y165C | W117R | >100 | 31 | No | No |

*26 tumours were noted in 22 cm of resected colon. The rest of the large bowel was not assessed.

```
SEQ ID No. 1: 347-1 G to A mutant sequence
The mutant base is indicated in bold and underlined
(Single letter amino acid sequence above and cDNA sequence
below. Lower case sequence represents non-coding intronic
sequence).
 M   T   P   L   V   S   R   L   S   R   L   W   A         13
ATG ACA CCG CTC GTC TCC CGC CTG AGT CGT CTG TGG GCC        39

I   M   R   K   P   R   A   A   V   G   S   G   H         26
ATC ATG AGG AAG CCA CGA GCA GCC GTG GGA AGT GGT CAC        78

R   K   Q   A   A   S   Q   E   G   R   Q   K   H         39
AGG AAG CAG GCA GCC AGC CAG GAA GGG AGG CAG AAG CAT       117

A   K   N   N   S   Q   A   K   P   S   A   C   D         52
GCT AAG AAC AAC AGT CAG GCC AAG CCT TCT GCC TGT GAT       156

G   L   A   R   Q   P   E   E   V   V   L   Q   A         65
GGC CTG GCC AGG CAG CCG GAA GAG GTG GTA TTG CAG GCC       195

S   V   S   S   Y   H   L   F   R   D   V   A   E         78
TCT GTC TCC TCA TAC CAT CTA TTC AGA GAC GTA GCT GAA       234

V   T   A   F   R   G   S   L   L   S   W   Y   D         91
GTC ACA GCC TTC CGA GGG AGC CTG CTA AGC TGG TAC GAC       273

Q   E   K   R   D   L   P   W   R   R   R   A   E        104
CAA GAG AAA CGG GAC CTA CCA TGG AGA AGA CGG GCA GAA       312

D   E   M   D   L   D   R   R   A   Y   A
GAT GAG ATG GAC CTG GAC AGG CGG GCA TAT GCT G . . . intron V   W                        117
aacccctttccccca<u>a</u>/TG TGG                              351

V   S   E   V   M   L   Q   Q   T   Q   V   A   T        130
GTC TCA GAG GTC ATG CTG CAG CAG ACC CAG GTT GCC ACT       390

V   I   N   Y   Y   T   G   W   M   Q   K   W   P        143
GTG ATC AAC TAC TAT ACC GGA TGG ATG CAG AAG TGG CCT       429

T   L   Q   D   L   A   S   A   S   L   E   E   V        156
ACA CTG CAG GAC CTG GCC AGT GCT TCC CTG GAG GAG GTG       468

N   Q   L   W   A   G   L   G   Y   Y   S   R   G        169
AAT CAA CTC TGG GCT GGC CTG GGC TAC TAT TCT CGT GGC       507

R   R   L   Q   E   G   A   R   K   V   V   E   E        182
```

```
                                -continued
    CGG CGG CTG CAG GAG GGA GCT CGG AAG GTG GTA GAG GAG        546

L   G   G   H   M   P   R   T   A   E   T   L   Q         195
    CTA GGG GGC CAC ATG CCA CGT ACA GCA GAG ACC CTG CAG        585

Q   L   L   P   G   V   G   R   Y   T   A   G   A         208
    CAG CTC CTG CCT GGC GTG GGG CGC TAC ACA GCT GGG GCC        624

I   A   S   I   A   F   G   Q   A   T   G   V   V         221
    ATT GCC TCT ATC GCC TTT GGC CAG GCA ACC GGT GTG GTG        663

D   G   N   V   A   R   V   L   C   R   V   R   A         234
    GAT GGC AAC GTA GCA CGG GTG CTG TGC CGT GTC CGA GCC        702

I   G   A   D   P   S   S   T   L   V   S   Q   Q         247
    ATT GGT GCT GAT CCC AGC AGC ACC CTT GTT TCC CAG CAG        741

L   W   G   L   A   Q   Q   L   V   D   P   A   R         260
    CTC TGG GGT CTA GCC CAG CAG CTG GTG GAC CCA GCC CGG        780

P   G   D   F   N   Q   A   A   M   E   L   G   A         273
    CCA GGA GAT TTC AAC CAA GCA GCC ATG GAG CTA GGG GCC        819

T   V   C   T   P   Q   R   P   L   C   S   Q   C         286
    ACA GTG TGT ACC CCA CAG CGC CCA CTG TGC AGC CAG TGC        858

P   V   E   S   L   C   R   A   R   Q   R   V   E         299
    CCT GTG GAG AGC CTG TGC CGG GCA CGC CAG AGA GTG GAG        897

Q   E   Q   L   L   A   S   G   S   L   S   G   S         312
    CAG GAA CAG CTC TTA GCC TCA GGG AGC CTG TCG GGC AGT        936

P   D   V   E   E   C   A   P   N   T   G   Q   C         325
    CCT GAC GTG GAG GAG TGT GCT CCC AAC ACT GGA CAG TGC        975

H   L   C   L   P   P   S   E   P   W   D   Q   T         338
    CAC CTG TGC CTG CCT CCC TCG GAG CCC TGG GAC CAG ACC       1014

L   G   V   V   N   F   P   R   K   A   S   R   K         351
    CTG GGA GTG GTC AAC TTC CCC AGA AAG GCC AGC CGC AAG       1053

P   P   R   E   E   S   S   A   T   C   V   L   E         364
    CCC CCC AGG GAG GAG AGC TCT GCC ACC TGT GTT CTG GAA       1092

Q   P   G   A   L   G   A   Q   I   L   L   V   Q         377
    CAG CCT GGG GCC CTT GGG GCC CAA ATT CTG CTG GTG CAG       1131

R   P   N   S   G   L   L   A   G   L   W   E   F         390
    AGG CCC AAC TCA GGT CTG CTG GCA GGA CTG TGG GAG TTC       1170

P   S   V   T   W   E   P   S   E   Q   L   Q   R         403
    CCG TCC GTG ACC TGG GAG CCC TCA GAG CAG CTT CAG CGC       1209

K   A   L   L   Q   E   L   Q   R   W   A   G   P         416
    AAG GCC CTG CTG CAG GAA CTA CAG CGT TGG GCT GGG CCC       1248

L   P   A   T   H   L   R   H   L   G   E   V   V         429
    CTC CCA GCC ACG CAC CTC CGG CAC CTT GGG GAG GTT GTC       1287

H   T   F   S   H   I   K   L   T   Y   Q   V   Y         442
    CAC ACC TTC TCT CAC ATC AAG CTG ACA TAT CAA GTA TAT       1326

G   L   A   L   E   G   Q   T   P   V   T   T   V         455
    GGG CTG GCC TTG GAA GGG CAG ACC CCA GTG ACC ACC GTA       1365

P   P   G   A   R   W   L   T   Q   E   E   F   H         468
    CCA CCA GGT GCT CGC TGG CTG ACG CAG GAG GAA TTT CAC       1404

T   A   A   V   S   T   A   M   K   K   V   F   R         481
    ACC GCA GCT GTT TCC ACC GCC ATG AAA AAG GTT TTC CGT       1443

V   Y   Q   G   Q   Q   P   G   T   C   M   G   S         494
    GTG TAT CAG GGC CAA CAG CCA GGG ACC TGT ATG GGT TCC       1482

K   R   S   Q   V   S   S   P   C   S   R   K   K         407
    AAA AGG TCC CAG GTG TCC TCT CCG TGC AGT CGG AAA AAG       1521

P   R   M   G   Q   Q   V   L   D   N   F   F   R         520
    CCC CGC ATG GGC CAG CAA GTC CTG GAT AAT TTC TTT CGG       1560
```

-continued

```
 S   H   I   S   T   D   A   H   S   L   N   S   A          533
TCT CAC ATC TCC ACT GAT GCA CAC AGC CTC AAC AGT GCA         1599

A   Q   *                                                  535
GCC CAG TGA                                                 1608
```

SEQ ID No: 2: 891 + 3 A to C
The mutant base is indicated in bold and underlined
(Single letter amino acid sequence above and cDNA sequence
below. Lower case sequence represents non-coding intronic
sequence).

```
 M   T   P   L   V   S   R   L   S   R   L   W   A          13
ATG ACA CCG CTC GTC TCC CGC CTG AGT CGT CTG TGG GCC         39

I   M   R   K   P   R   A   A   V   G   S   G   H          26
ATC ATG AGG AAG CCA CGA GCA GCC GTG GGA AGT GGT CAC         78

R   K   Q   A   A   S   Q   E   G   R   Q   K   H          39
AGG AAG CAG GCA GCC AGC CAG GAA GGG AGG CAG AAG CAT         117

A   K   N   N   S   Q   A   K   P   S   A   C   D          52
GCT AAG AAC AAC AGT CAG GCC AAG CCT TCT GCC TGT GAT         156

G   L   A   R   Q   P   E   E   V   V   L   Q   A          65
GGC CTG GCC AGG CAG CCG GAA GAG GTG GTA TTG CAG GCC         195

S   V   S   S   Y   H   L   F   R   D   V   A   E          78
TCT GTC TCC TCA TAC CAT CTA TTC AGA GAC GTA GCT GAA         234

V   T   A   F   R   G   S   L   L   S   W   Y   D          91
GTC ACA GCC TTC CGA GGG AGC CTG CTA AGC TGG TAC GAC         273

Q   E   K   R   D   L   P   W   R   R   A   E             104
CAA GAG AAA CGG GAC CTA CCA TGG AGA AGA CGG GCA GAA         312

D   E   M   D   L   D   R   R   A   Y   A   V   W         117
GAT GAG ATG GAC CTG GAC AGG CGG GCA TAT GCT GTG TGG         351

V   S   E   V   M   L   Q   Q   T   Q   V   A   T         130
GTC TCA GAG GTC ATG CTG CAG CAG ACC CAG GTT GCC ACT         390

V   I   N   Y   Y   T   G   W   M   Q   K   W   P         143
GTG ATC AAC TAC TAT ACC GGA TGG ATG CAG AAG TGG CCT         429

T   L   Q   D   L   A   S   A   S   L   E   E   V         156
ACA CTG CAG GAC CTG GCC AGT GCT TCC CTG GAG GAG GTG         468

N   Q   L   W   A   G   L   G   Y   Y   S   R   G         169
AAT CAA CTC TGG GCT GGC CTG GGC TAC TAT TCT CGT GGC         507

R   R   L   Q   E   G   A   R   K   V   V   E   E         182
CGG CGG CTG CAG GAG GGA GCT CGG AAG GTG GTA GAG GAG         546

L   G   G   H   M   P   R   T   A   E   T   L   Q         195
CTA GGG GGC CAC ATG CCA CGT ACA GCA GAG ACC CTG CAG         585

Q   L   L   P   G   V   G   R   Y   T   A   G   A         208
CAG CTC CTG CCT GGC GTG GGG CGC TAC ACA GCT GGG GCC         624

I   A   S   I   A   F   G   Q   A   T   G   V   V         221
ATT GCC TCT ATC GCC TTT GGC CAG GCA ACC GGT GTG GTG         663

D   G   N   V   A   R   V   L   C   R   V   R   A         234
GAT GGC AAC GTA GCA CGG GTG CTG TGC CGT GTC CGA GCC         702

I   G   A   D   P   S   S   T   L   V   S   Q   Q         247
ATT GGT GCT GAT CCC AGC AGC ACC CTT GTT TCC CAG CAG         741

L   W   G   L   A   Q   Q   L   V   D   P   A   R         260
CTC TGG GGT CTA GCC CAG CAG CTG GTG GAC CCA GCC CGG         780

P   G   D   F   N   Q   A   A   M   E   L   G   A         273
CCA GGA GAT TTC AAC CAA GCA GCC ATG GAG CTA GGG GCC         819

T   V   C   T   P   Q   R   P   L   C   S   Q   C         286
ACA GTG TGT ACC CCA CAG CGC CCA CTG TGC AGC CAG TGC         858

P   V   E   S   L   C   R   A   R   Q   R
CCT GTG GAG AGC CTG TGC CGG GCA CGC CAG AGA/gtcagcctact
```

-continued

```
            V   E                                         299
intron/GTG GAG                                            897

Q   E   Q   L   L   A   S   G   S   L   S   G   S      312
CAG GAA CAG CTC TTA GCC TCA GGG AGC CTG TCG GGC AGT       936

P   D   V   E   E   C   A   P   N   T   G   Q   C      325
CCT GAC GTG GAG GAG TGT GCT CCC AAC ACT GGA CAG TGC       975

H   L   C   L   P   P   S   E   P   W   D   Q   T      338
CAC CTG TGC CTG CCT CCC TCG GAG CCC TGG GAC CAG ACC       1014

L   G   V   V   N   F   P   R   K   A   S   R   K      351
CTG GGA GTG GTC AAC TTC CCC AGA AAG GCC AGC CGC AAG       1053

P   P   R   E   E   S   S   A   T   C   V   L   E      364
CCC CCC AGG GAG GAG AGC TCT GCC ACC TGT GTT CTG GAA       1092

Q   P   G   A   L   G   A   Q   I   L   L   V   Q      377
CAG CCT GGG GCC CTT GGG GCC CAA ATT CTG CTG GTG CAG       1131

R   P   N   S   G   L   L   A   G   L   W   E   F      390
AGG CCC AAC TCA GGT CTG CTG GCA GGA CTG TGG GAG TTC       1170

P   S   V   T   W   E   P   S   E   Q   L   Q   R      403
CCG TCC GTG ACC TGG GAG CCC TCA GAG CAG CTT CAG CGC       1209

K   A   L   L   Q   E   L   Q   R   W   A   G   P      416
AAG GCC CTG CTG CAG GAA CTA CAG CGT TGG GCT GGG CCC       1248

L   P   A   T   H   L   R   H   L   G   E   V   V      429
CTC CCA GCC ACG CAC CTC CGG CAC CTT GGG GAG GTT GTC       1287

H   T   F   S   H   I   K   L   T   Y   Q   V   Y      442
CAC ACC TTC TCT CAC ATC AAG CTG ACA TAT CAA GTA TAT       1326

G   L   A   L   E   G   Q   T   P   V   T   T   V      455
GGG CTG GCC TTG GAA GGG CAG ACC CCA GTG ACC ACC GTA       1365

P   P   G   A   R   W   L   T   Q   E   E   F   H      468
CCA CCA GGT GCT CGC TGG CTG ACG CAG GAG GAA TTT CAC       1404

T   A   A   V   S   T   A   M   K   K   V   F   R      481
ACC GCA GCT GTT TCC ACC GCC ATG AAA AAG GTT TTC CGT       1443

V   Y   Q   G   Q   Q   P   G   T   C   M   G   S      494
GTG TAT CAG GGC CAA CAG CCA GGG ACC TGT ATG GGT TCC       1482

K   R   S   Q   V   S   S   P   C   S   R   K   K      407
AAA AGG TCC CAG GTG TCC TCT CCG TGC AGT CGG AAA AAG       1521

P   R   M   G   Q   Q   V   L   D   N   F   F   R      520
CCC CGC ATG GGC CAG CAA GTC CTG GAT AAT TTC TTT CGG       1560

S   H   I   S   T   D   A   H   S   L   N   S   A      533
TCT CAC ATC TCC ACT GAT GCA CAC AGC CTC AAC AGT GCA       1599

A   Q   *                                               535
GCC CAG TGA                                               1608
```

SEQ ID No: 3: Q324X (C to T at nucleotide 970)
The mutant codon and amino acid indicated in bold and under-
lined (Single letter amino acid sequence above and cDNA
sequence below).

```
  M   T   P   L   V   S   R   L   S   R   L   W   A      13
ATG ACA CCG CTC GTC TCC CGC CTG AGT CGT CTG TGG GCC       39

I   M   R   K   P   R   A   A   V   G   S   G   H      26
ATC ATG AGG AAG CCA CGA GCA GCC GTG GGA AGT GGT CAC       78

R   K   Q   A   A   S   Q   E   G   R   Q   K   H      39
AGG AAG CAG GCA GCC AGC CAG GAA GGG AGG CAG AAG CAT       117

A   K   N   N   S   Q   A   K   P   S   A   C   D      52
GCT AAG AAC AAC AGT CAG GCC AAG CCT TCT GCC TGT GAT       156

G   L   A   R   Q   P   E   E   V   V   L   Q   A      65
GGC CTG GCC AGG CAG CCG GAA GAG GTG GTA TTG CAG GCC       195

S   V   S   S   Y   H   L   F   R   D   V   A   E      78
```

-continued

```
              TCT GTC TCC TCA TAC CAT CTA TTC AGA GAC GTA GCT GAA       234

V   T   A   F   R   G   S   L   L   S   W   Y   D            91
GTC ACA GCC TTC CGA GGG AGC CTG CTA AGC TGG TAC GAC             273

Q   E   K   R   D   L   P   W   R   R   R   A   E           104
CAA GAG AAA CGG GAC CTA CCA TGG AGA AGA CGG GCA GAA             312

D   E   M   D   L   D   R   R   A   Y   A   V   W           117
GAT GAG ATG GAC CTG GAC AGG CGG GCA TAT GCT GTG TGG             351

V   S   E   V   M   L   Q   Q   T   Q   V   A   T           130
GTC TCA GAG GTC ATG CTG CAG CAG ACC CAG GTT GCC ACT             390

V   I   N   Y   Y   T   G   W   M   Q   K   W   P           143
GTG ATC AAC TAC TAT ACC GGA TGG ATG CAG AAG TGG CCT             429

T   L   Q   D   L   A   S   A   S   L   E   E   V           156
ACA CTG CAG GAC CTG GCC AGT GCT TCC CTG GAG GAG GTG             468

N   Q   L   W   A   G   L   G   Y   Y   S   R   G           169
AAT CAA CTC TGG GCT GGC CTG GGC TAC TAT TCT CGT GGC             507

R   R   L   Q   E   G   A   R   K   V   V   E   E           182
CGG CGG CTG CAG GAG GGA GCT CGG AAG GTG GTA GAG GAG             546

L   G   G   H   M   P   R   T   A   E   T   L   Q           195
CTA GGG GGC CAC ATG CCA CGT ACA GCA GAG ACC CTG CAG             585

Q   L   L   P   G   V   G   R   Y   T   A   G   A           208
CAG CTC CTG CCT GGC GTG GGG CGC TAC ACA GCT GGG GCC             624

I   A   S   I   A   F   G   Q   A   T   G   V   V           221
ATT GCC TCT ATC GCC TTT GGC CAG GCA ACC GGT GTG GTG             663

D   G   N   V   A   R   V   L   C   R   V   R   A           234
GAT GGC AAC GTA GCA CGG GTG CTG TGC CGT GTC CGA GCC             702

I   G   A   D   P   S   S   T   L   V   S   Q   Q           247
ATT GGT GCT GAT CCC AGC AGC ACC CTT GTT TCC CAG CAG             741

L   W   G   L   A   Q   Q   L   V   D   P   A   R           260
CTC TGG GGT CTA GCC CAG CAG CTG GTG GAC CCA GCC CGG             780

P   G   D   F   N   Q   A   A   M   E   L   G   A           273
CCA GGA GAT TTC AAC CAA GCA GCC ATG GAG CTA GGG GCC             819

T   V   C   T   P   Q   R   P   L   C   S   Q   C           286
ACA GTG TGT ACC CCA CAG CGC CCA CTG TGC AGC CAG TGC             858

P   V   E   S   L   C   R   A   R   Q   R   V   E           299
CCT GTG GAG AGC CTG TGC CGG GCA CGC CAG AGA GTG GAG             897

Q   E   Q   L   L   A   S   G   S   L   S   G   S           312
CAG GAA CAG CTC TTA GCC TCA GGG AGC CTG TCG GGC AGT             936

P   D   V   E   E   C   A   P   N   T   G   X   C           325
CCT GAC GTG GAG GAG TGT GCT CCC AAC ACT GGA TAG TGC         975

H   L   C   L   P   P   S   E   P   W   D   Q   T           338
CAC CTG TGC CTG CCT CCC TCG GAG CCC TGG GAC CAG ACC             1014

L   G   V   V   N   F   P   R   K   A   S   R   K           351
CTG GGA GTG GTC AAC TTC CCC AGA AAG GCC AGC CGC AAG             1053

P   P   R   E   E   S   S   A   T   C   V   L   E           364
CCC CCC AGG GAG GAG AGC TCT GCC ACC TGT GTT CTG GAA             1092

Q   P   G   A   L   G   A   Q   I   L   L   V   Q           377
CAG CCT GGG GCC CTT GGG GCC CAA ATT CTG CTG GTG CAG             1131

R   P   N   S   G   L   L   A   G   L   W   E   F           390
AGG CCC AAC TCA GGT CTG CTG GCA GGA CTG TGG GAG TTC             1170

P   S   V   T   W   E   P   S   E   Q   L   Q   R           403
CCG TCC GTG ACC TGG GAG CCC TCA GAG CAG CTT CAG CGC             1209

K   A   L   L   Q   E   L   Q   R   W   A   G   P           416
AAG GCC CTG CTG CAG GAA CTA CAG CGT TGG GCT GGG CCC             1248
```

-continued

```
     L    P    A    T    H    L    R    H    L    G    E    V    V         429
     CTC  CCA  GCC  ACG  CAC  CTC  CGG  CAC  CTT  GGG  GAG  GTT  GTC        1287

H    T    F    S    H    I    K    L    T    Y    Q    V    Y         442
     CAC  ACC  TTC  TCT  CAC  ATC  AAG  CTG  ACA  TAT  CAA  GTA  TAT        1326

G    L    A    L    E    G    Q    T    P    V    T    T    V         455
     GGG  CTG  GCC  TTG  GAA  GGG  CAG  ACC  CCA  GTG  ACC  ACC  GTA        1365

P    P    G    A    R    W    L    T    Q    E    E    F    H         468
     CCA  CCA  GGT  GCT  CGC  TGG  CTG  ACG  CAG  GAG  GAA  TTT  CAC        1404

T    A    A    V    S    T    A    M    K    K    V    F    R         481
     ACC  GCA  GCT  GTT  TCC  ACC  GCC  ATG  AAA  AAG  GTT  TTC  CGT        1443

V    Y    Q    G    Q    Q    P    G    T    C    M    G    S         494
     GTG  TAT  CAG  GGC  CAA  CAG  CCA  GGG  ACC  TGT  ATG  GGT  TCC        1482

K    R    S    Q    V    S    S    P    C    S    R    K    K         407
     AAA  AGG  TCC  CAG  GTG  TCC  TCT  CCG  TGC  AGT  CGG  AAA  AAG        1521

P    R    M    G    Q    Q    V    L    D    N    F    F    R         520
     CCC  CGC  ATG  GGC  CAG  CAA  GTC  CTG  GAT  AAT  TTC  TTT  CGG        1560

S    H    I    S    T    D    A    H    S    L    N    S    A         533
     TCT  CAC  ATC  TCC  ACT  GAT  GCA  CAC  AGC  CTC  AAC  AGT  GCA        1599

A    Q    *                                                            535
     GCC  CAG  TGA                                                          1608
```

SEQ ID No. 4: W117R (T to A at nucleotide 349)
The mutant codon and amino acid indicated in bold and underlined (Single letter amino acid sequence above and cDNA sequence below).

```
     M    T    P    L    V    S    R    L    S    R    L    W    A         13
     ATG  ACA  CCG  CTC  GTC  TCC  CGC  CTG  AGT  CGT  CTG  TGG  GCC        39

I    M    R    K    P    R    A    A    V    G    S    G    H         26
     ATC  ATG  AGG  AAG  CCA  CGA  GCA  GCC  GTG  GGA  AGT  GGT  CAC        78

R    K    Q    A    A    S    Q    E    G    R    Q    K    H         39
     AGG  AAG  CAG  GCA  GCC  AGC  CAG  GAA  GGG  AGG  CAG  AAG  CAT        117

A    K    N    N    S    Q    A    K    P    S    A    C    D         52
     GCT  AAG  AAC  AAC  AGT  CAG  GCC  AAG  CCT  TCT  GCC  TGT  GAT        156

G    L    A    R    Q    P    E    E    V    V    L    Q    A         65
     GGC  CTG  GCC  AGG  CAG  CCG  GAA  GAG  GTG  GTA  TTG  CAG  GCC        195

S    V    S    S    Y    H    L    F    R    D    V    A    E         78
     TCT  GTC  TCC  TCA  TAC  CAT  CTA  TTC  AGA  GAC  GTA  GCT  GAA        234

V    T    A    F    R    G    S    L    L    S    W    Y    D         91
     GTC  ACA  GCC  TTC  CGA  GGG  AGC  CTG  CTA  AGC  TGG  TAC  GAC        273

Q    E    K    R    D    L    P    W    R    R    A    E             104
     CAA  GAG  AAA  CGG  GAC  CTA  CCA  TGG  AGA  AGA  CGG  GCA  GAA        312

D    E    M    D    L    D    R    R    A    Y    A    V    R    117
     GAT  GAG  ATG  GAC  CTG  GAC  AGG  CGG  GCA  TAT  GCT  GTG  AGG   351

V    S    E    V    M    L    Q    Q    T    Q    V    A    T         130
     GTC  TCA  GAG  GTC  ATG  CTG  CAG  CAG  ACC  CAG  GTT  GCC  ACT        390

V    I    N    Y    Y    T    G    W    M    Q    K    W    P         143
     GTG  ATC  AAC  TAC  TAT  ACC  GGA  TGG  ATG  CAG  AAG  TGG  CCT        429

T    L    Q    D    L    A    S    A    S    L    E    E    V         156
     ACA  CTG  CAG  GAC  CTG  GCC  AGT  GCT  TCC  CTG  GAG  GAG  GTG        468

N    Q    L    W    A    G    L    G    Y    Y    S    R    G         169
     AAT  CAA  CTC  TGG  GCT  GGC  CTG  GGC  TAC  TAT  TCT  CGT  GGC        507

R    R    L    Q    E    G    A    R    K    V    V    E    E         182
     CGG  CGG  CTG  CAG  GAG  GGA  GCT  CGG  AAG  GTG  GTA  GAG  GAG        546

L    G    G    H    M    P    R    T    A    E    T    L    Q         195
     CTA  GGG  GGC  CAC  ATG  CCA  CGT  ACA  GCA  GAG  ACC  CTG  CAG        585

Q    L    L    P    G    V    G    R    Y    T    A    G    A         208
```

```
                    -continued
     CAG CTC CTG CCT GGC GTG GGG CGC TAC ACA GCT GGG GCC              624

I   A   S   I   A   F   G   Q   A   T   G   V   V        221
     ATT GCC TCT ATC GCC TTT GGC CAG GCA ACC GGT GTG GTG              663

D   G   N   V   A   R   V   L   C   R   V   R   A        234
     GAT GGC AAC GTA GCA CGG GTG CTG TGC CGT GTC CGA GCC              702

I   G   A   D   P   S   S   T   L   V   S   Q   Q        247
     ATT GGT GCT GAT CCC AGC AGC ACC CTT GTT TCC CAG CAG              741

L   W   G   L   A   Q   Q   L   V   D   P   A   R        260
     CTC TGG GGT CTA GCC CAG CAG CTG GTG GAC CCA GCC CGG              780

P   G   D   F   N   Q   A   A   M   E   L   G   A        273
     CCA GGA GAT TTC AAC CAA GCA GCC ATG GAG CTA GGG GCC              819

T   V   C   T   P   Q   R   P   L   C   S   Q   C        286
     ACA GTG TGT ACC CCA CAG CGC CCA CTG TGC AGC CAG TGC              858

P   V   E   S   L   C   R   A   R   Q   R   V   E        299
     CCT GTG GAG AGC CTG TGC CGG GCA CGC CAG AGA GTG GAG              897

Q   E   Q   L   L   A   S   G   S   L   S   G   S        312
     CAG GAA CAG CTC TTA GCC TCA GGG AGC CTG TCG GGC AGT              936

P   D   V   E   E   C   A   P   N   T   G   Q   C        325
     CCT GAC GTG GAG GAG TGT GCT CCC AAC ACT GGA CAG TGC              975

H   L   C   L   P   P   S   E   P   W   D   Q   T        338
     CAC CTG TGC CTG CCT CCC TCG GAG CCC TGG GAC CAG ACC             1014

L   G   V   V   N   F   P   R   K   A   S   R   K        351
     CTG GGA GTG GTC AAC TTC CCC AGA AAG GCC AGC CGC AAG             1053

P   P   R   E   E   S   S   A   T   C   V   L   E        364
     CCC CCC AGG GAG GAG AGC TCT GCC ACC TGT GTT CTG GAA             1092

Q   P   G   A   L   G   A   Q   I   L   L   V   Q        377
     CAG CCT GGG GCC CTT GGG GCC CAA ATT CTG CTG GTG CAG             1131

R   P   N   S   G   L   L   A   G   L   W   E   F        390
     AGG CCC AAC TCA GGT CTG CTG GCA GGA CTG TGG GAG TTC             1170

P   S   V   T   W   E   P   S   E   Q   L   Q   R        403
     CCG TCC GTG ACC TGG GAG CCC TCA GAG CAG CTT CAG CGC             1209

K   A   L   L   Q   E   L   Q   R   W   A   G   P        416
     AAG GCC CTG CTG CAG GAA CTA CAG CGT TGG GCT GGG CCC             1248

L   P   A   T   H   L   R   H   L   G   E   V   V        429
     CTC CCA GCC ACG CAC CTC CGG CAC CTT GGG GAG GTT GTC             1287

H   T   F   S   H   I   K   L   T   Y   Q   V   Y        442
     CAC ACC TTC TCT CAC ATC AAG CTG ACA TAT CAA GTA TAT             1326

G   L   A   L   E   G   Q   T   P   V   T   T   V        455
     GGG CTG GCC TTG GAA GGG CAG ACC CCA GTG ACC ACC GTA             1365

P   P   G   A   R   W   L   T   Q   E   E   F   H        468
     CCA CCA GGT GCT CGC TGG CTG ACG CAG GAG GAA TTT CAC             1404

T   A   A   V   S   T   A   M   K   K   V   F   R        481
     ACC GCA GCT GTT TCC ACC GCC ATG AAA AAG GTT TTC CGT             1443

V   Y   Q   G   Q   Q   P   G   T   C   M   G   S        494
     GTG TAT CAG GGC CAA CAG CCA GGG ACC TGT ATG GGT TCC             1482

K   R   S   Q   V   S   S   P   C   S   R   K   K        407
     AAA AGG TCC CAG GTG TCC TCT CCG TGC AGT CGG AAA AAG             1521

P   R   M   G   Q   Q   V   L   D   N   F   F   R        520
     CCC CGC ATG GGC CAG CAA GTC CTG GAT AAT TTC TTT CGG             1560

S   H   I   S   T   D   A   H   S   L   N   S   A        533
     TCT CAC ATC TCC ACT GAT GCA CAC AGC CTC AAC AGT GCA             1599

A   Q   *                                                 535
     GCC CAG TGA                                                     1608
```

What is claimed is:

1. An isolated nucleic acid comprising a contiguous span of at least 19 nucleotide residues of an MYH nucleic acid, at least one of which nucleotide residues being a nucleotide variant selected from the group consisting of 347−1 G to A corresponding to position 7084 of SEQ ID NO:1, 891+3 A to C corresponding to position 8092 of SEQ ID NO:2, 970 C to T corresponding to position 970 of SEQ ID NO:3 and 349 T to A corresponding to position 349 of SEQ ID NO:4, or the complement of said nucleic acid.

2. The isolated nucleic acid of claim 1, wherein said nucleotide variant is at the 5' or 3' end of said contiguous span.

3. The isolated nucleic acid of claim 1, wherein said nucleotide variant is within no more than 3 nucleotides of the center of said contiguous span.

4. The isolated nucleic acid of claim 1, wherein said contiguous span comprises at least 20 nucleotide residues of said MYH nucleic acid.

5. The isolated nucleic acid of claim 4, wherein the nucleotide variant is at the 5' or 3' end of said contiguous span.

6. The isolated nucleic acid of claim 4, wherein said nucleotide variant is within no more than 3 nucleotides of the center of said contiguous span.

7. The isolated nucleic acid of claim 4, wherein said nucleotide variant is 347−1 G to A corresponding to position 7084 of SEQ ID NO:1.

8. The isolated nucleic acid of claim 4, wherein said nucleotide variant is 891+3 A to C corresponding to position 8092 of SEQ ID NO:2.

9. The isolated nucleic acid of claim 4, wherein said nucleotide variant is 970 C to T corresponding to position 970 of SEQ ID NO:3.

10. The isolated nucleic acid of claim 4, wherein said nucleotide variant is 349 T to A corresponding to position 349 of SEQ ID NO:4.

11. The isolated nucleic acid of claim 1, wherein said contiguous span comprises at least 25 nucleotide residues of said MYH nucleic acid.

12. The isolated nucleic acid of claim 11, wherein the nucleotide variant is at the 5' or 3' end of said contiguous span.

13. The isolated nucleic acid of claim 11, wherein the nucleotide variant is within no more than 3 nucleotides of the center of said contiguous span.

14. The isolated nucleic acid of claim 1, wherein said contiguous span comprises at least 30 nucleotide residues of said MYH nucleic acid.

15. The isolated nucleic acid of claim 1, wherein said contiguous span comprises at least 50 nucleotide residues of said MYH nucleic acid.

16. A microchip comprising the isolated nucleic acid of claim 1.

17. An isolated MYH nucleic acid containing at least one nucleotide variant selected from the group consisting of 970 C to T corresponding to position 970 of SEQ ID NO:3 and 349 T to A corresponding to position 349 of SEQ ID NO:4, or the complement of said nucleic acid.

18. The isolated MYH nucleic acid of claim 17 or said complement thereof, wherein said isolated MYH nucleic acid encodes a protein having an amino acid sequence at least 95% identical to SEQ ID NO:3 wherein the amino acid sequence contains the amino acid variant Q324X.

19. The isolated MYH nucleic acid of claim 17 or said complement thereof, wherein said isolated MYH nucleic acid encodes a protein having an amino acid sequence at least 97% identical to SEQ ID NO:3 wherein the amino acid sequence contains the amino acid variant Q324X.

20. The isolated MYH nucleic acid of claim 17 or said complement thereof, wherein said isolated MYH nucleic acid encodes a protein having an amino acid sequence according to SEQ ID NO:3 wherein the amino acid sequence contains the amino acid variant Q324X.

21. The isolated MYH nucleic acid of claim 17 or said complement thereof, wherein said isolated MYH nucleic acid encodes a protein having an amino acid sequence at least 95% identical to SEQ ID NO:4 wherein the amino acid sequence contains the amino acid variant W117R.

22. The isolated MYH nucleic acid of claim 17 or said complement thereof, wherein said isolated MYH nucleic acid encodes a protein having an amino acid sequence at least 97% identical to SEQ ID NO:4 wherein the amino acid sequence contains the amino acid variant W117R.

23. The isolated MYH nucleic acid of claim 17 or said complement thereof, wherein said isolated MYH nucleic acid encodes a protein having an amino acid sequence according to SEQ ID NO:4 wherein the amino acid sequence contains the amino acid variant W117R.

24. An isolated nucleic acid encoding a contiguous span of at least 7 amino acid residues of an MYH protein, wherein said contiguous span contains at least one amino acid variant selected from the group consisting of Q324X and W117R, or the complement of said nucleic acid.

25. The isolated nucleic acid of claim 24 or the complement thereof, wherein said contiguous span comprises at least 10 amino acid residues of said MYH protein.

26. An isolated oligonucleotide comprising a contiguous span of at least 19 nucleotides of the sequence of a mutant MYH gene, wherein said contiguous span contains a genetic variant selected from the group consisting of 347−1 G to A corresponding to position 7084 of SEQ ID NO:1, 891+3 A to C corresponding to position 8092 of SEQ ID NO:2, 970 C to T corresponding to position 970 of SEQ ID NO:3 and 349 T to A corresponding to position 349 of SEQ ID NO:4.

27. The isolated oligonucleotide of claim 26, wherein the genetic variant is 347−1 G to A corresponding to position 7084 of SEQ ID NO:1.

28. The isolated oligonucleotide of claim 26, wherein the genetic variant is 891+3 A to C corresponding to position 8092 of SEQ ID NO:2.

29. The isolated oligonucleotide of claim 26, wherein the genetic variant is 970 C to T corresponding to position 970 of SEQ ID NO:3.

30. The isolated oligonucleotide of claim 26, wherein the genetic variant is 349 T to A corresponding to position 349 of SEQ ID NO:4.

31. A detection kit comprising the isolated oligonucleotide according to claim 26.

* * * * *

UNITED STATES PATENT AND TRADEMARK OFFICE
CERTIFICATE OF CORRECTION

PATENT NO. : 7,393,940 B2
APPLICATION NO. : 11/247968
DATED : July 1, 2008
INVENTOR(S) : Sampson et al.

It is certified that error appears in the above-identified patent and that said Letters Patent is hereby corrected as shown below:

Column 81, line 25, cancel the text beginning with "1. An isolated nucleic acid" to and ending "nucleic acid." in column 81, line 33, and insert the following claim:

--1. An isolated MYH nucleic acid comprising a contiguous span of at least 19 nucleotides, wherein said contiguous span contains a single genetic variant selected from the group consisting of G to A at position 7084 of SEQ ID NO:1, A to C at position 8092 of SEQ ID NO:2, C to T at position 970 of SEQ ID NO:3 and T to A at position 349 of SEQ ID NO:4, or the full complement of said isolated nucleic acid.--

Column 82, line 32, cancel the text beginning with "17. An isolated MYH" to and ending "nucleic acid." in column 82, line 36, and insert the following claim:

--17. An isolated MYH nucleic acid containing at least one single-nucleotide variant selected from the group consisting of C to T at position 970 of SEQ ID NO:3 and T to A at position 349 of SEQ ID NO:4, or the full complement of said isolated nucleic acid.--

Column 83, line 1, cancel the text beginning with "24. An isolated nucleic acid" to and ending "nucleic acid." in column 83, line 5, and insert the following claim:

--24. An isolated MYH nucleic acid encoding a contiguous span of at least 7 amino acid residues, wherein said contiguous span contains at least one amino acid variant selected from the group consisting of Q324X and W117R, or the full complement of said isolated nucleic acid.--

UNITED STATES PATENT AND TRADEMARK OFFICE
CERTIFICATE OF CORRECTION

| | |
|---|---|
| PATENT NO. | : 7,393,940 B2 |
| APPLICATION NO. | : 11/247968 |
| DATED | : July 1, 2008 |
| INVENTOR(S) | : Sampson et al. |

It is certified that error appears in the above-identified patent and that said Letters Patent is hereby corrected as shown below:

Column 83, line 9, cancel the text beginning with "26. An isolated oligonucleotide" to and ending "SEQ ID NO:4." in column 83, line 16, and insert the following claim:

--26. An isolated MYH nucleic acid comprising a contiguous span of at least 19 nucleotides of the sequence of a mutant MYH gene, wherein said contiguous span contains a single genetic variant selected from the group consisting of G to A at position 7084 of SEQ ID NO:1, A to C at position 8092 of SEQ ID NO:2, C to T at position 970 if SEQ ID NO:3, and T to A at position 349 of SEQ ID NO:4, or the full complement of said isolated nucleic acid.--

Signed and Sealed this

Twenty-fourth Day of March, 2009

JOHN DOLL
*Acting Director of the United States Patent and Trademark Office*